US012731218B2

(12) United States Patent
Sasai et al.

(10) Patent No.: US 12,731,218 B2
(45) Date of Patent: Sep. 8, 2026

(54) LEARNING SUPPORT DEVICE, ENDOSCOPE SYSTEM, AND METHOD FOR SUPPORTING LEARNING

(71) Applicants: OLYMPUS CORPORATION, Tokyo (JP); National Cancer Center, Tokyo (JP)

(72) Inventors: Ryota Sasai, Tokyo (JP); Masaaki Ito, Tokyo (JP); Atsushi Yamada, Tokyo (JP); Hiroki Matsuzaki, Tokyo (JP); Hiro Hasegawa, Tokyo (JP); Kazuyuki Hayashi, Tokyo (JP); Yuki Furusawa, Tokyo (JP)

(73) Assignees: OLYMPUS CORPORATION, Tokyo (JP); NATIONAL CANCER CENTER, Tokyo (JP)

( * ) Notice: Subject to any disclaimer, the term of this patent is extended or adjusted under 35 U.S.C. 154(b) by 147 days.

(21) Appl. No.: 18/614,838

(22) Filed: Mar. 25, 2024

(65) Prior Publication Data

US 2024/0331098 A1 Oct. 3, 2024

Related U.S. Application Data

(60) Provisional application No. 63/455,041, filed on Mar. 28, 2023.

(51) Int. Cl.
*G06T 5/50* (2006.01)
*G06T 5/92* (2024.01)
(Continued)

(52) U.S. Cl.
CPC .................. *G06T 5/50* (2013.01); *G06T 5/92* (2024.01); *G06T 7/194* (2017.01); *G06V 10/60* (2022.01);
(Continued)

(58) Field of Classification Search
CPC .. G06T 5/50; G06T 7/194; G06T 5/92; G06T 2207/10068; G06T 2207/20221; G16H 30/40; G06V 10/60
See application file for complete search history.

(56) References Cited

U.S. PATENT DOCUMENTS 7,791,651 B2 * 9/2010 Donomae ................ G06T 5/94 382/254
8,882,662 B2 11/2014 Charles
(Continued)

FOREIGN PATENT DOCUMENTS

JP 2012120702 A 6/2012
WO 2019/058300 A1 3/2019

OTHER PUBLICATIONS

Y. Mochizuki, "CV & Technologies_Normalizeimage brightness", Retrieved from the Internet, Mar. 31, 2017, URL:https://cvtech.cc/std/.
(Continued)

*Primary Examiner* — Xiao M Wu
*Assistant Examiner* — Ryan Allen Barham
(74) *Attorney, Agent, or Firm* — Scully, Scott, Murphy & Presser, P.C.

(57) ABSTRACT

A learning support device includes a processor. The processor is configured to: form a foreground image containing at least one treatment instrument by placing an image of the at least one treatment instrument within an image region; form a superimposed image by superimposing the foreground image on a background image; and form a training image by adjusting at least one of hue, saturation, or brightness of the superimposed image.

9 Claims, 22 Drawing Sheets

(51) Int. Cl.

| | |
|---|---|
| ***G06T 7/194*** | (2017.01) |
| ***G06V 10/60*** | (2022.01) |
| ***G16H 30/40*** | (2018.01) |

(52) U.S. Cl.

CPC ... *G16H 30/40* (2018.01); *G06T 2207/10068* (2013.01); *G06T 2207/20221* (2013.01)

(56) References Cited

U.S. PATENT DOCUMENTS

| | | | | |
|---|---|---|---|---|
| 9,216,068 | B2 | 12/2015 | Tesar | |
| 9,492,065 | B2 | 11/2016 | Tesar et al. | |
| 9,615,728 | B2 | 4/2017 | Charles et al. | |
| 9,629,523 | B2 | 4/2017 | Tesar et al. | |
| 9,936,863 | B2 | 4/2018 | Tesar | |
| 10,022,041 | B2 | 7/2018 | Charles et al. | |
| 10,231,607 | B2 | 3/2019 | Charles et al. | |
| 10,614,346 | B2 | 4/2020 | Inoue | |
| 11,166,706 | B2 | 11/2021 | Charles et al. | |
| 11,450,079 | B2 * | 9/2022 | Usuda | A61B 1/000094 |
| 11,451,698 | B2 | 9/2022 | Kikuchi et al. | |
| 11,889,976 | B2 | 2/2024 | Charles et al. | |
| 12,582,288 | B2 | 3/2026 | Charles et al. | |
| 2010/0295931 | A1 | 11/2010 | Schmidt | |
| 2015/0051617 | A1 | 2/2015 | Takemura et al. | |
| 2016/0350912 | A1 | 12/2016 | Koide et al. | |
| 2019/0087694 | A1 | 3/2019 | Inoue | |
| 2020/0082229 | A1 | 3/2020 | Inoue | |
| 2020/0175343 | A1 | 6/2020 | Inoue | |
| 2020/0372668 | A1 * | 11/2020 | Lin | G06N 3/08 |
| 2021/0209398 | A1 | 7/2021 | Endo | |
| 2021/0319539 | A1 | 10/2021 | Agarwal et al. | |
| 2022/0172828 | A1 | 6/2022 | Qiu et al. | |
| 2023/0009051 | A1 | 1/2023 | Goto | |
| 2024/0371060 | A1 | 11/2024 | Buschle et al. | |
| 2026/0007302 | A1 | 1/2026 | Takenouchi | |

OTHER PUBLICATIONS

U.S. Appl. No. 18/614,942.

US Office Action dated Apr. 3, 2026 received in U.S. Appl. No. 18/614,942.

Jin Yueming, et al.,“Incorporating Temporal Prior from Motion Flow for Instrument Segmentation in Minimally Invasive Surgery Video”, Cornell University, pp. 3-9; arXiv:1907.07899v1 [cs.CV] Jul. 18, 2019.

* cited by examiner 100
14
13
12
12a
11
16
X

A1
A2
A3
16a
16b
16c
A1a
A3a
A3b
B
Ba
C
D
E
F
J

A1
A2
A3
16a
16b
16c
A1a
A3a
A3b
C
J
F
C'
Ba
B

B
D
E
Ba
16c
16a
C
F
J
2
CAD DATA
CAD DATA
CAD DATA
I1
I2
I3

FIG. 17

LEARNING SUPPORT DEVICE, ENDOSCOPE SYSTEM, AND METHOD FOR SUPPORTING LEARNING

CROSS-REFERENCE TO RELATED APPLICATIONS

This application claims the benefit of U.S. Provisional Application No. 63/455,041, filed Mar. 28, 2023, which is incorporated by reference herein in its entirety.

TECHNICAL FIELD

The present invention relates to a learning support device, an endoscope system, and a method for supporting learning.

BACKGROUND ART

In an endoscope system, a technique to automatically recognize treatment instruments within an endoscopic image is used. An example of a technique to recognize treatment instruments includes a method that uses deep learning, and deep learning requires a large number of training images.

There is also a known technique to form a training image from two images. For example, U.S. Pat. No. 10,614,346 discloses that intensities of respective pixels in a first image and a second image are simply averaged to form a training image.

SUMMARY OF INVENTION

One aspect of the present invention is a learning support device that supports formation of a learning model that recognizes a treatment instrument within an endoscopic image, the learning support device including a processor, wherein the processor is configured to: form a foreground image containing at least one treatment instrument by placing an image of the at least one treatment instrument within an image region; form a superimposed image by superimposing the foreground image on a background image; and form a training image by adjusting at least one of hue, saturation, or brightness of the superimposed image.

Another aspect of the present invention is a learning support device that supports formation of a learning model that recognizes a treatment instrument within an endoscopic image, the learning support device including a processor, wherein the processor is configured to: form a foreground image containing at least one treatment instrument by placing an image of the at least one treatment instrument within an image region; adjust at least one of hue, saturation, or brightness of the foreground image; and form a training image by superimposing the foreground image, which is adjusted, on a background image.

Another aspect of the present invention is an endoscope system including: the above-mentioned learning support device; an endoscope configured to acquire an endoscopic image; and an image processing apparatus including a processor and a storage unit configured to store the learning model, wherein the processor of the image processing apparatus is configured to input the endoscopic image to the learning model to obtain, from the learning model, a recognition result with respect to the treatment instrument within the endoscopic image.

Another aspect of the present invention is to a method for supporting learning, the method supporting formation of a learning model that recognizes a treatment instrument within an endoscopic image, the method including: forming a foreground image containing at least one treatment instrument by placing an image of the at least one treatment instrument within an image region; forming a superimposed image by superimposing the foreground image on a background image; and forming a training image by adjusting at least one of hue, saturation, or brightness of the superimposed image.

BRIEF DESCRIPTION OF DRAWINGS

FIG. 17 is a flowchart of a method for supporting learning according to the fourth embodiment.

DESCRIPTION OF EMBODIMENTS

First Embodiment

A learning support device and a method for supporting learning according to a first embodiment of the present invention will be described with reference to drawings.

A learning support device 10 according to the present embodiment supports formation of a learning model that recognizes treatment instruments within an endoscopic image. To be more specific, the learning support device 10 forms training images necessary to form a learning model.

Figure 1:
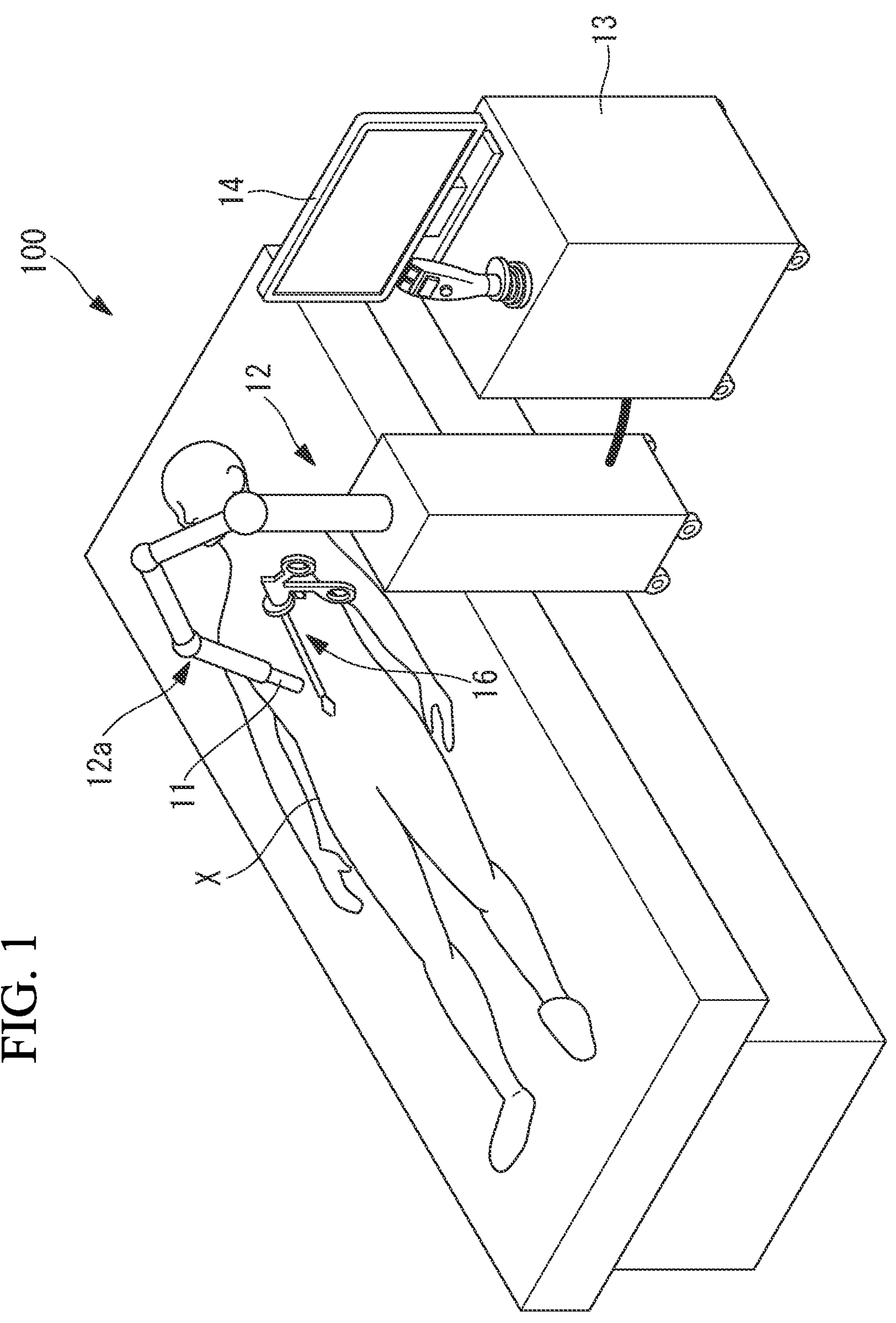
FIG. 1 is an overall configuration diagram showing an example of an endoscope system in which a learning support device is used.

FIG. 1 shows an example of an endoscope system 100 in which a learning model formed by the learning support device 10 is used. The endoscope system 100 includes an endoscope 11, a moving device 12 that changes a position and an orientation of the endoscope 11, a control device 13, and a display device 14. The endoscope system 100 is used for surgery in which the endoscope 11 and a treatment instrument 16 are inserted into a body of a patient as a subject X to treat a part to be treated with the treatment instrument 16 while the treatment instrument 16 is observed by the endoscope 11. For example, the endoscope system 100 is used for laparoscopic surgery.

Figure 2A:
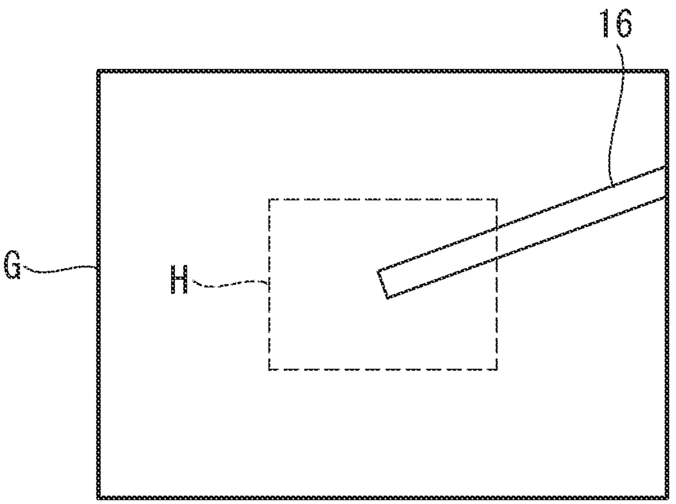
FIG. 2A is a diagram showing an endoscopic image to illustrate tracking control.
Figure 2B:
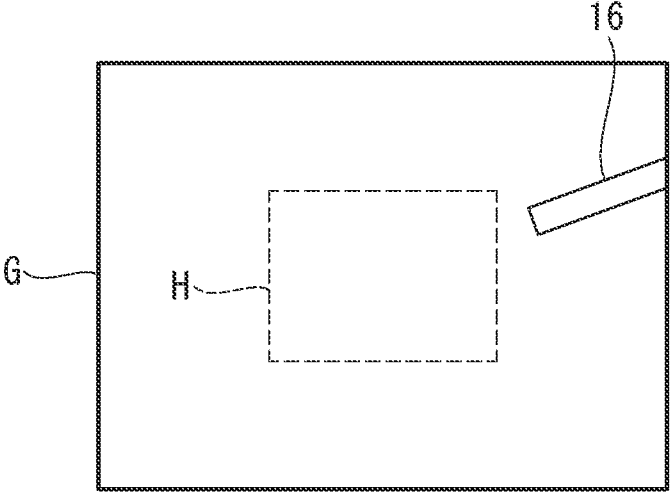
FIG. 2B is a diagram showing an endoscopic image to illustrate the tracking control.

The control device 13 performs tracking control that causes a field of view of the endoscope 11 to track the treatment instrument 16 by controlling the moving device 12 based on a position of the treatment instrument 16. FIG. 2A and FIG. 2B show examples of the tracking control. In these examples, the moving device 12 is controlled such that a distal end of the treatment instrument 16 is placed within a predetermined specified region H within an endoscopic image G. That is, when the distal end is located within the specified region H, the endoscope 11 is not moved (see FIG. 2A). In contrast, when the distal end is located outside the specified region H, the endoscope 11 is moved in such a way as to cause the distal end to be within the specified region H (see FIG. 2B).

The learning model is used to recognize the treatment instrument 16 as the target to be tracked within the endoscopic image G during tracking control, for example.

Figure 3:
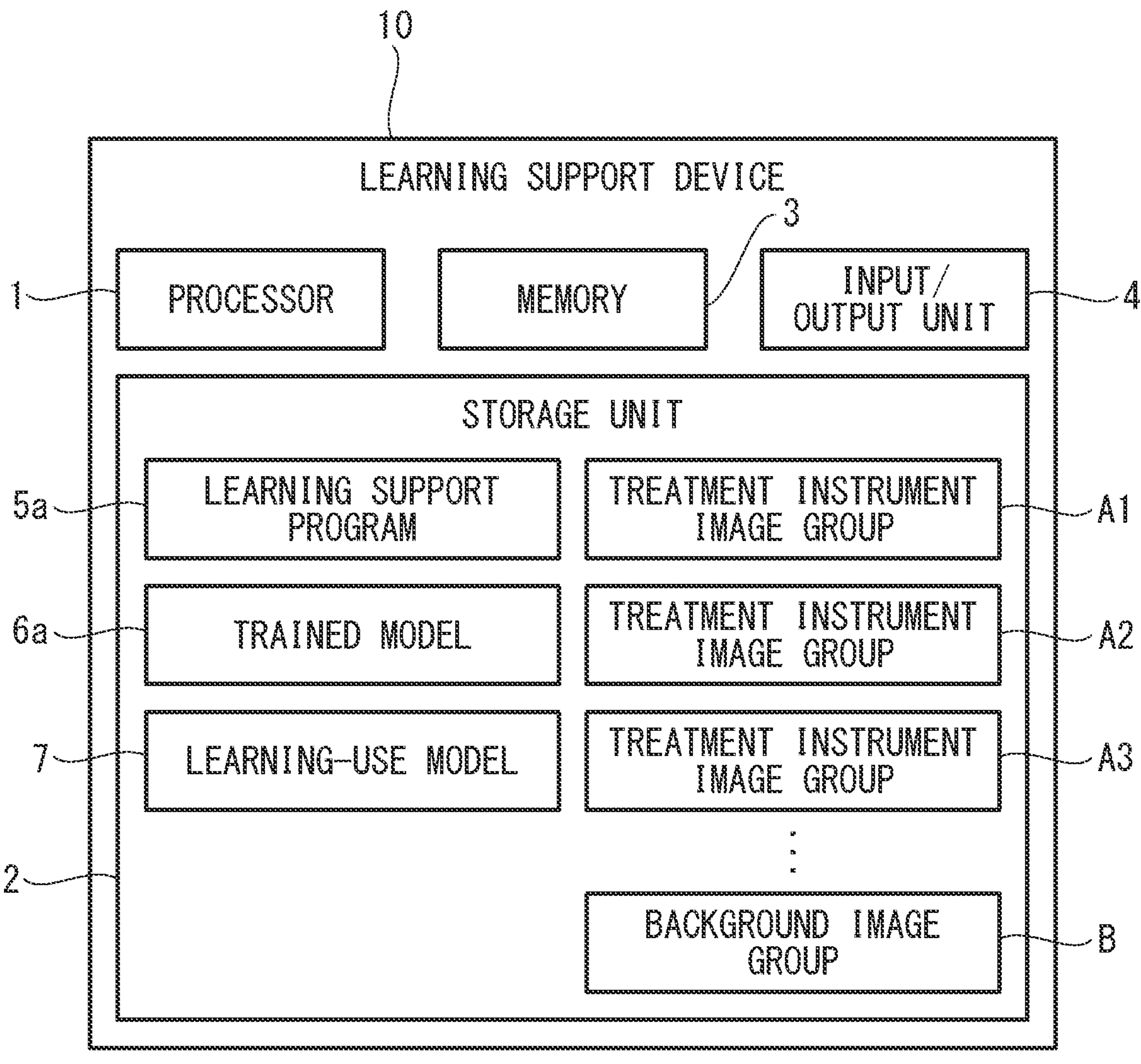
FIG. 3 is a block diagram showing a configuration of the learning support device according to a first embodiment.

As shown in FIG. 3, the learning support device 10 includes a processor 1, such as a central processing unit, a storage unit 2, a memory 3, and an input/output unit 4.

The storage unit 2 is a computer readable non-transitory recording medium, and may be a hard disk drive, an optical disk, or a flash memory, for example. The storage unit 2 stores a learning support program 5*a* that causes the processor 1 to perform a method for supporting learning according to the present embodiment, which will be described later. The storage unit 2 further stores sample image groups A1, A2, A3, . . . , B and trained model 6*a*, all of which are necessary for the method for supporting learning.

The processor 1 forms a training image E from the sample image groups A1, A2, A3, . . . , B according to the learning support program 5*a* that is read into the memory 3, such as a RAM (random access memory), from the storage unit 2.

The input/output unit 4 has a known input interface and a known output interface.

The sample image groups A1, A2, A3, . . . , B are images of objects that may appear in a clinical image. The clinical image is an endoscopic image acquired by the endoscope 11 during actual endoscopic surgery. In the present embodiment, sample image groups include a plurality of treatment instrument image groups A1, A2, A3, . . . , and a background image group B.

Each of the treatment instrument image groups A1, A2, A3, . . . is formed of a plurality of treatment instrument images containing treatment instrument 16*a*, 16*b*, 16*c*, . . . , and the treatment instruments 16*a*, 16*b*, 16*c*, . . . differ from each other.

The plurality of treatment instrument images of the treatment instrument image group A1 are a plurality of color images that differ from each other in distance in a depth direction (that is, size) and posture of the treatment instrument 16*a*. For example, the plurality of treatment instrument images are obtained by photographing, by an endoscope, the treatment instrument 16*a* placed on an arbitrary background at various distances and in various postures. In the same manner, the plurality of treatment instrument images of each of other treatment instrument image groups A2, A3, are also a plurality of color images that differ from each other in distance and posture of the treatment instrument 16*b*, 16*c*, . . . .

The background image group B is formed of a plurality of color background images that differ from each other. A background image is an image of an organ, and is obtained by photographing various positions in an abdominal cavity at various angles by the endoscope, for example.

The trained model 6*a* is a GAN (Generative Adversarial Networks) that forms a training image E (described later) from a superimposed image D (described later) based on the relationship, learned in advance, between the color of a superimposed image and the color of a clinical image, at least the colors of treatment instruments being adjusted in the training image E. The trained model 6*a* is preferably a CycleGAN. As will be described later, the trained model 6*a* according to the present embodiment is a CycleGAN that is trained to convert the colors of treatment instruments and an organ within a superimposed image to colors close to those of treatment instruments and an organ within a clinical image. The trained model 6*a* may be a GAN of another kind, such as a DCGAN (Deep Convolutional GAN), an LSGAN (Least Square GAN), a Wasserstein GAN, or a PGGAN (Progressive Growing GAN), for example.

As used herein, “color” refers to saturation, hue, and brightness being three elements of color, and “adjust color” means to adjust at least one of saturation, hue, or brightness.

Next, the method for supporting learning that is performed by the learning support device 10 will be described.

Figure 4:
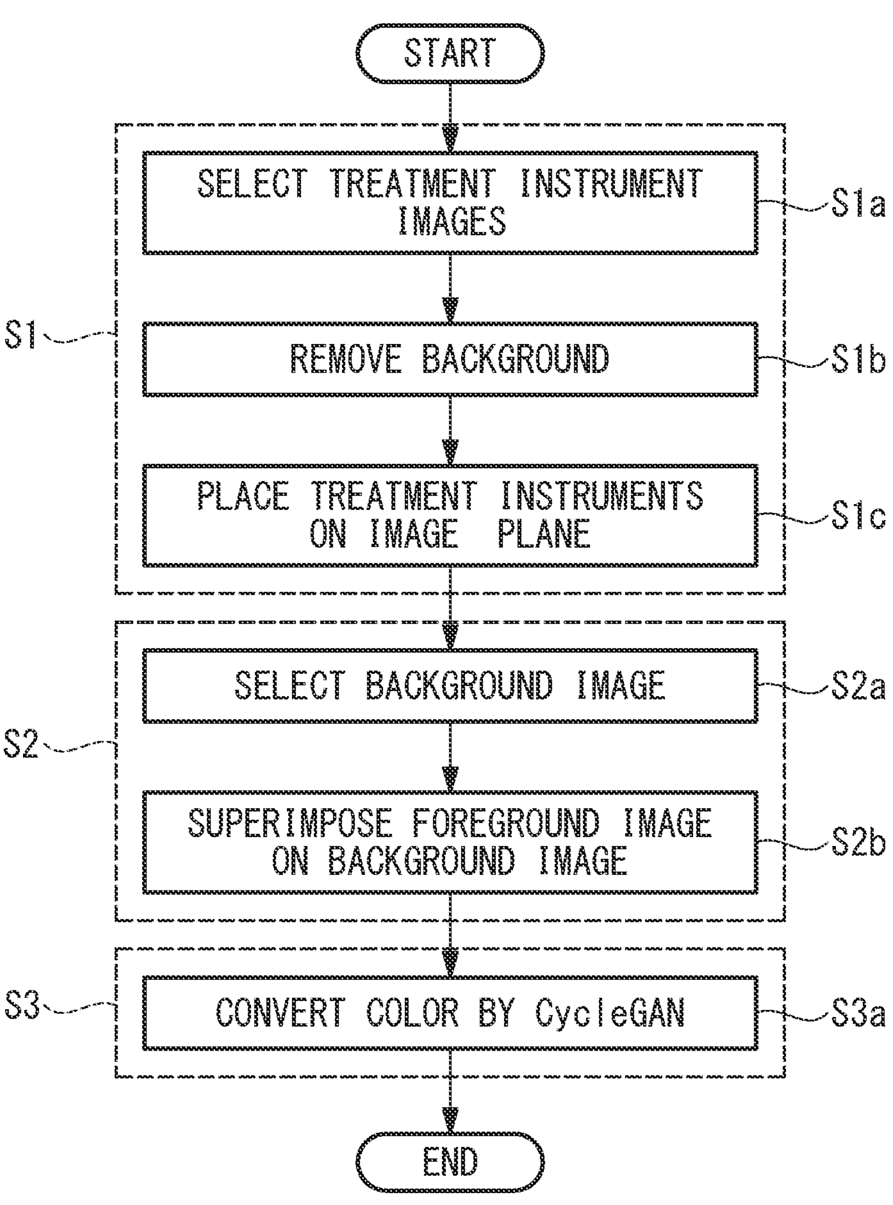
FIG. 4 is a flowchart of a method for supporting learning according to the first embodiment.

As shown in FIG. 4, the method for supporting learning according to the present embodiment includes step S1 of forming a foreground image C containing at least one treatment instrument, step S2 of forming a superimposed image D in which the foreground image C is superimposed on a background image, and step S3 of forming a training image E by adjusting at least one of the hue, the saturation, or the brightness of the superimposed image D.

Figure 5:
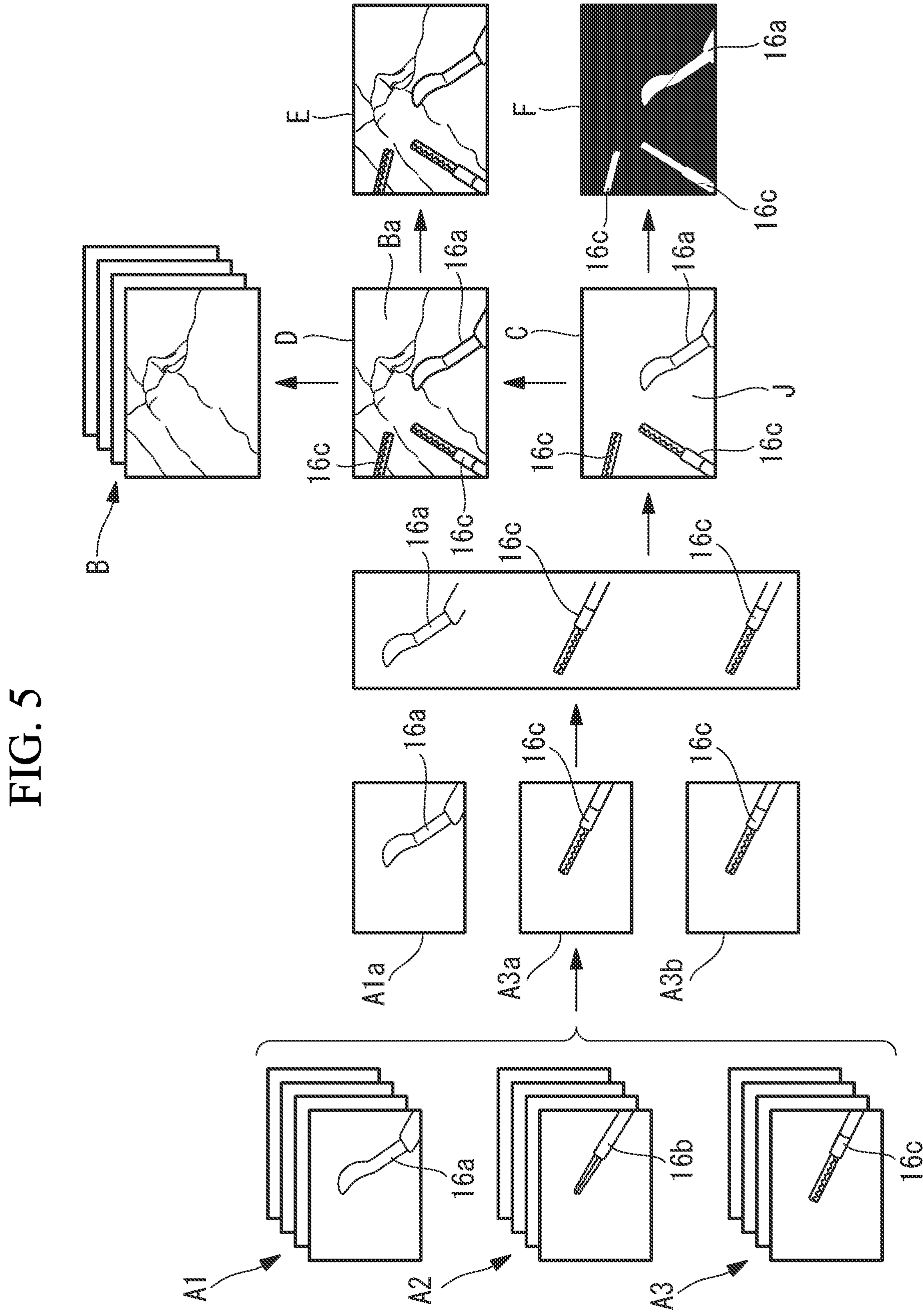
FIG. 5 is a diagram illustrating the method for supporting learning shown in FIG. 4.

FIG. 5 illustrates image processing in the method for supporting learning according to the present embodiment.

In step S1, the processor 1 selects at least one treatment instrument image from the plurality of treatment instrument image groups A1, A2, A3, . . . (step S1*a*). In the case of the example shown in FIG. 5, one treatment instrument image A1*a* is selected from the first treatment instrument image group A1, and two treatment instrument images A3*a*, A3*b* are selected from the third treatment instrument image group A3.

The processor 1 may determine the kind and the number of treatment instruments according to placement data stored in advance in the storage unit 2, and may select at least one treatment instrument image based on the determined kind and number of treatment instruments.

The placement data specifies the three-dimensional placement of at least one treatment instrument within the foreground image C, and may be created based on the three-dimensional placement that may actually occur during endoscopic surgery with respect to the treatment instruments within a clinical image. For example, placement data includes information on the number of treatment instruments, the kind of each treatment instrument, and the three-dimensional position and orientation of each treatment instrument, within the foreground image C.

Next, the processor 1 removes a background of each of the selected treatment instrument images A1a, A3a, A3b to extract an image of the treatment instrument 16a, 16c within the treatment instrument image A1a, A3a, A3b (step S1b). Next, the processor 1 places the images of the treatment instruments 16a, 16c within a two-dimensional image region J, thus forming the foreground image C (step S1c). The processor 1 may place the treatment instruments 16a, 16c in an image region J at random or according to the placement data.

In the following step S2, the processor 1 selects any one background image Ba from the background image group B (step S2a), and forms a superimposed image D by superimposing the foreground image C on the background image Ba (step S2b).

In the following step S3, the processor 1 inputs the superimposed image D to the CycleGAN 6a, and then obtains, as an output from the CycleGAN 6a, a training image E being an image in which the hue, the saturation, and the brightness of the treatment instruments 16a, 16c, and the organ within the superimposed image D are converted (step S3a).

The CycleGAN is trained to form an image similar to the clinical image from the superimposed image D by using a plurality of superimposed images D experimentally formed and a plurality of clinical images. Accordingly, the CycleGAN 6a forms, from the superimposed image D, the training image E with reality, that is, the training image E in which the hue, the saturation, and the brightness of the treatment instruments 16a, 16c, and the organ are close to those in the clinical image.

By performing steps S1 to S3 a large number of times, the processor 1 can form a large number of training images E that differ from each other in the number, kind, position and orientation of treatment instruments.

As described above, according to the present embodiment, the training image E is formed from the image groups A1, A2, A3, . . . , B, and a clinical image containing treatment instruments is not required. Accordingly, it is possible to form a training image E for various treatment instruments, including a treatment instrument for which there are no or only a small number of clinical images and hence, it is possible to support formation of a learning model for various treatment instruments, including the treatment instrument for which there are no or only a small number of clinical images.

The colors of treatment instruments within the treatment instrument image differ from the colors of treatment instruments within the clinical image due to the influence from the colors of a background, illumination light, or the like. Thus, there is a deviation between the superimposed image D and the clinical image with respect to the colors of the treatment instruments.

According to the present embodiment, by adjusting the hue, the saturation, and the brightness of the treatment instruments within the superimposed image D based on the relationship, learned in advance, between the color of the superimposed image and the color of the clinical image, it is possible to form a training image E with reality, that is, a training image E with small deviation from the clinical image with respect to color. By learning such a training image E, it is possible to form a learning model with high recognition accuracy for treatment instruments within the clinical image and hence, recognition performance for treatment instruments within an endoscopic image during endoscopic surgery can be enhanced.

Further, according to the present embodiment, not only the hue, the saturation, and the brightness of treatment instruments, but also the hue, the saturation, and the brightness of an organ being a background are also adjusted. Thus, it is possible to form a training image E with high reality of both treatment instruments and the background.

Further, according to the present embodiment, the GAN 6a is used as means for adjusting the color of the superimposed image D and hence, it is possible to form, from any treatment instrument image, a training image E with high reality of treatment instruments.

Further, a superimposed image and a clinical image used for training of the CycleGAN 6a are not always necessarily a pair of images in which the shape, position, and the like of treatment instruments strictly coincide with each other, and various superimposed images and various clinical images may be used for training. Accordingly, it is possible to easily prepare images necessary for training of the CycleGAN 6a.

In the present embodiment, the processor 1 adjusts the color of the superimposed image D. However, the processor 1 may adjust the color of the foreground image C instead of adjusting the color of the superimposed image D. This method is also able to form a training image E with reality close to the clinical image.

Figure 6:
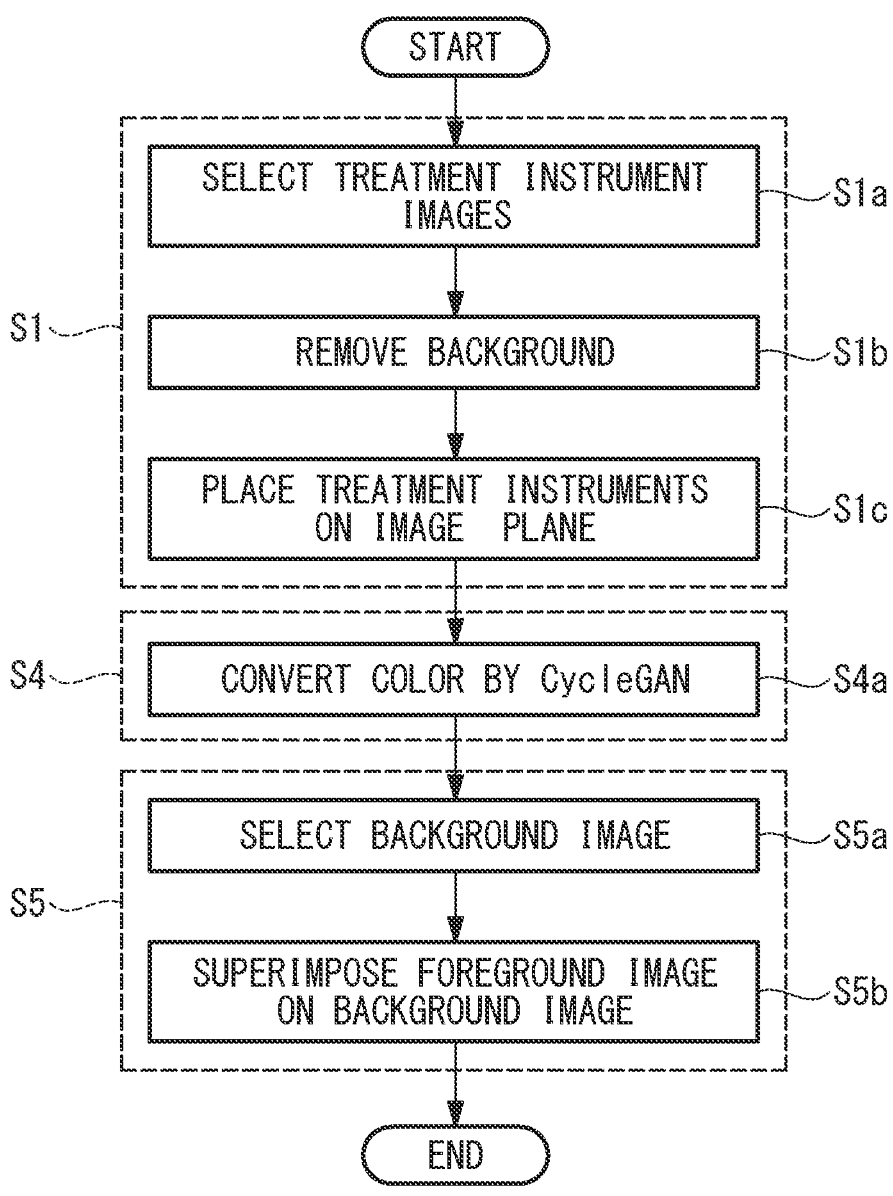
FIG. 6 is a flowchart of a modification of the method for supporting learning according to the first embodiment.
Figure 7:
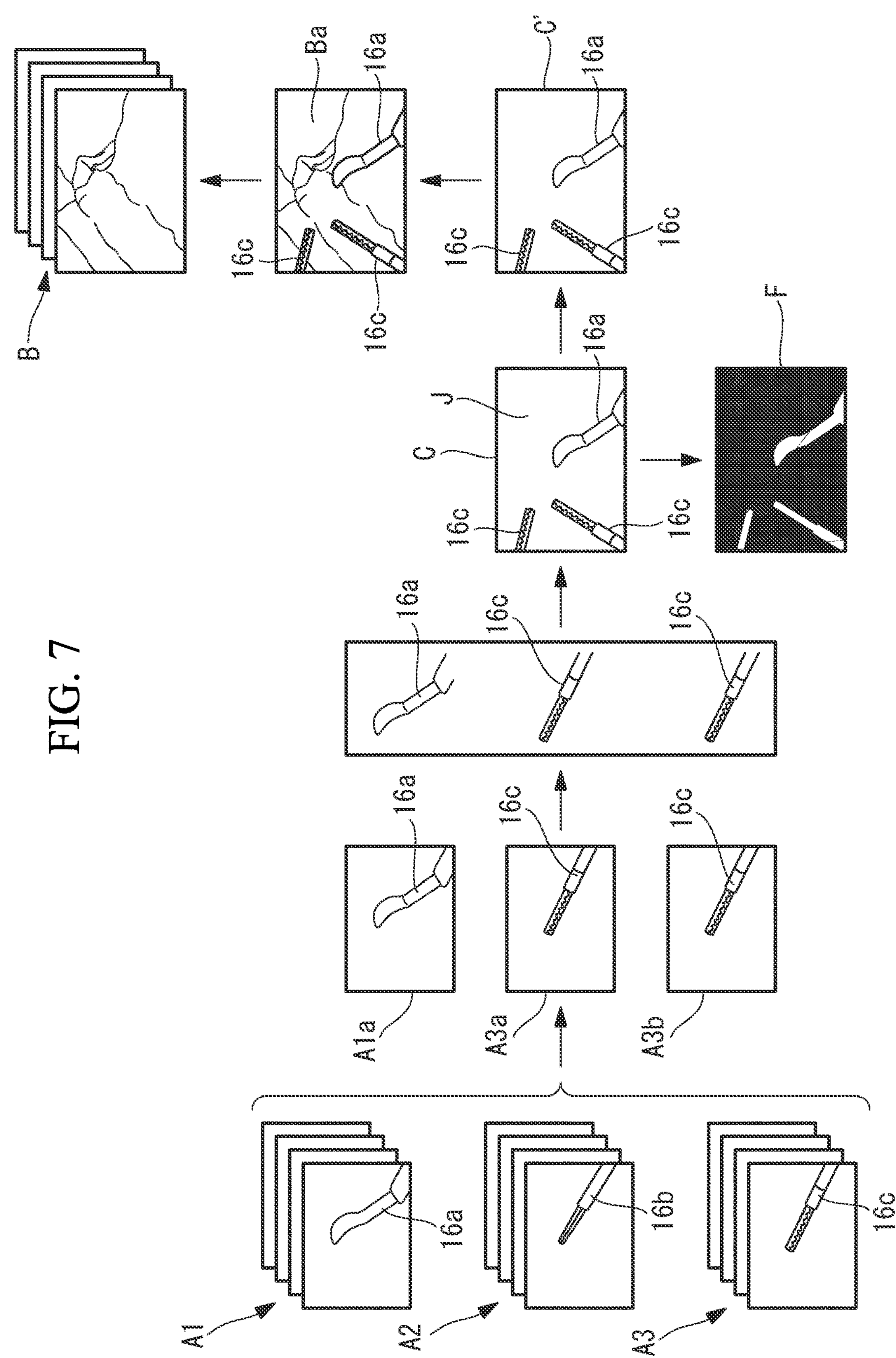
FIG. 7 is a diagram illustrating the method for supporting learning shown in FIG. 6.

FIG. 6 and FIG. 7 illustrate formation of the training image E in the case in which the color of the foreground image C is adjusted.

Instead of steps S2 and S3, the method for supporting learning shown in FIG. 6 includes step S4 of adjusting the color of the foreground image C, and step S5 of forming a training image E by superimposing the foreground image C' with the adjusted color on a background image.

In step S4, the processor 1 forms the image C' in which the colors of treatment instruments within the foreground image C are converted (adjusted) by the CycleGAN 6a (step S4a). In this case, the CycleGAN 6a is used that is trained to convert the colors of treatment instruments within the foreground image C to colors close to those of treatment instruments within the clinical image by using images of treatment instruments cut out from the clinical image.

Next, in step S5, the processor 1 forms a training image E by superimposing the foreground image C' on the background image Ba, which is selected (steps S5a, S5b).

Figure 8:
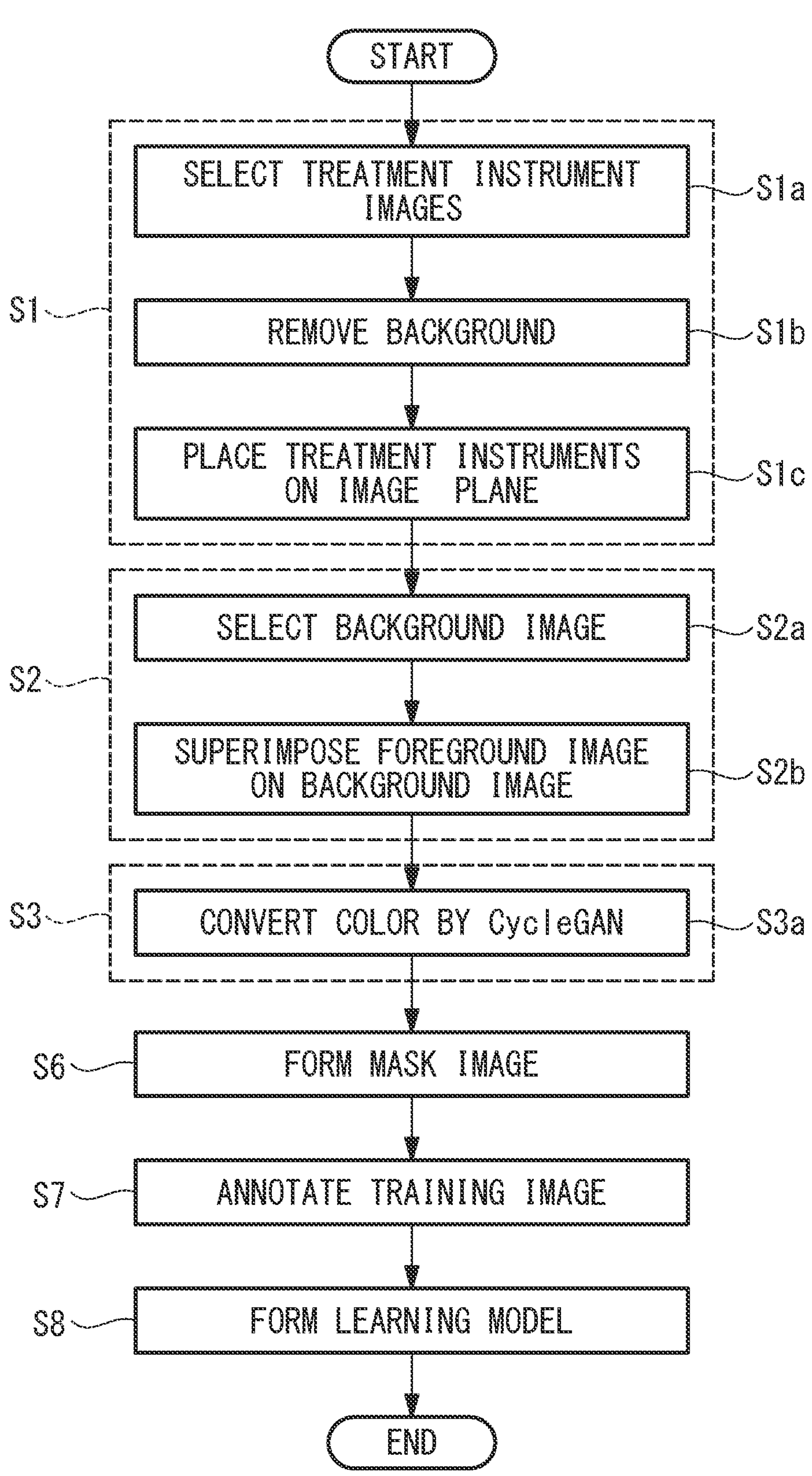
FIG. 8 is a flowchart of another modification of the method for supporting learning according to the first embodiment.

As shown in FIG. 8, the method for supporting learning of the present embodiment may further include step S6 of forming a mask image F based on the foreground image C, and step S7 of annotating the training image E based on the mask image F.

The timing of each of steps S6, S7 shown in FIG. 8 is merely an example, and may be suitably changed.

As shown in FIGS. 5 and 7, the mask image F is an image obtained by extracting only the regions of the treatment instruments 16a, 16c within the foreground image C. In step S7, the processor 1 selects, from the training image E, regions at the same positions as the regions of the treatment instruments 16a, 16c within the mask image F, and labels the positions of the selected regions to the training image E as information on the positions of the regions of the treatment instruments.

To form a learning model that recognizes treatment instruments, it is necessary to perform annotation in which information on the positions of the regions of the treatment instruments is labeled to each training image E. By automatically annotating the training image E by forming the mask image F from the foreground image C, it is possible to cause the processor 1 to perform annotation of a large number of training images E. Further, the positions of the regions of the treatment instruments within the foreground image C coincide with the positions of the regions of the treatment instruments within the training image E and hence, by using the mask image F formed from the foreground image C, it is possible to accurately annotate the training image E.

As shown in FIG. 8, the method for supporting learning of the present embodiment may further include step S8 of learning a plurality of training images E to form a learning model that recognizes treatment instruments within the endoscopic image. In this case, the storage unit 2 further stores a learning-use model 7 that forms a learning model by learning the training image E (see FIG. 3).

After performing annotation, the processor 1 causes the learning-use model 7 to learn annotated training images E, thus causing the learning-use model 7 to form a learning model.

Such a configuration allows the learning support device 10 to perform the whole process from formation of a training image E to formation of a learning model.

Although FIG. 8 shows an example of the method for supporting learning shown in FIG. 4, the method for supporting learning shown in FIG. 6 may also further include steps S6, S7, and S8.

Second Embodiment

Next, a learning support device and a method for supporting learning according to a second embodiment of the present invention will be described.

The present embodiment differs from the first embodiment with respect to a point that a foreground image C is formed from CG (computer graphics) instead of treatment instrument images. In the present embodiment, components that are different from the components in the first embodiment will be described. Components identical to the corresponding components in the first embodiment are given the same reference symbols, and the description of such components will be omitted.

Figure 9:
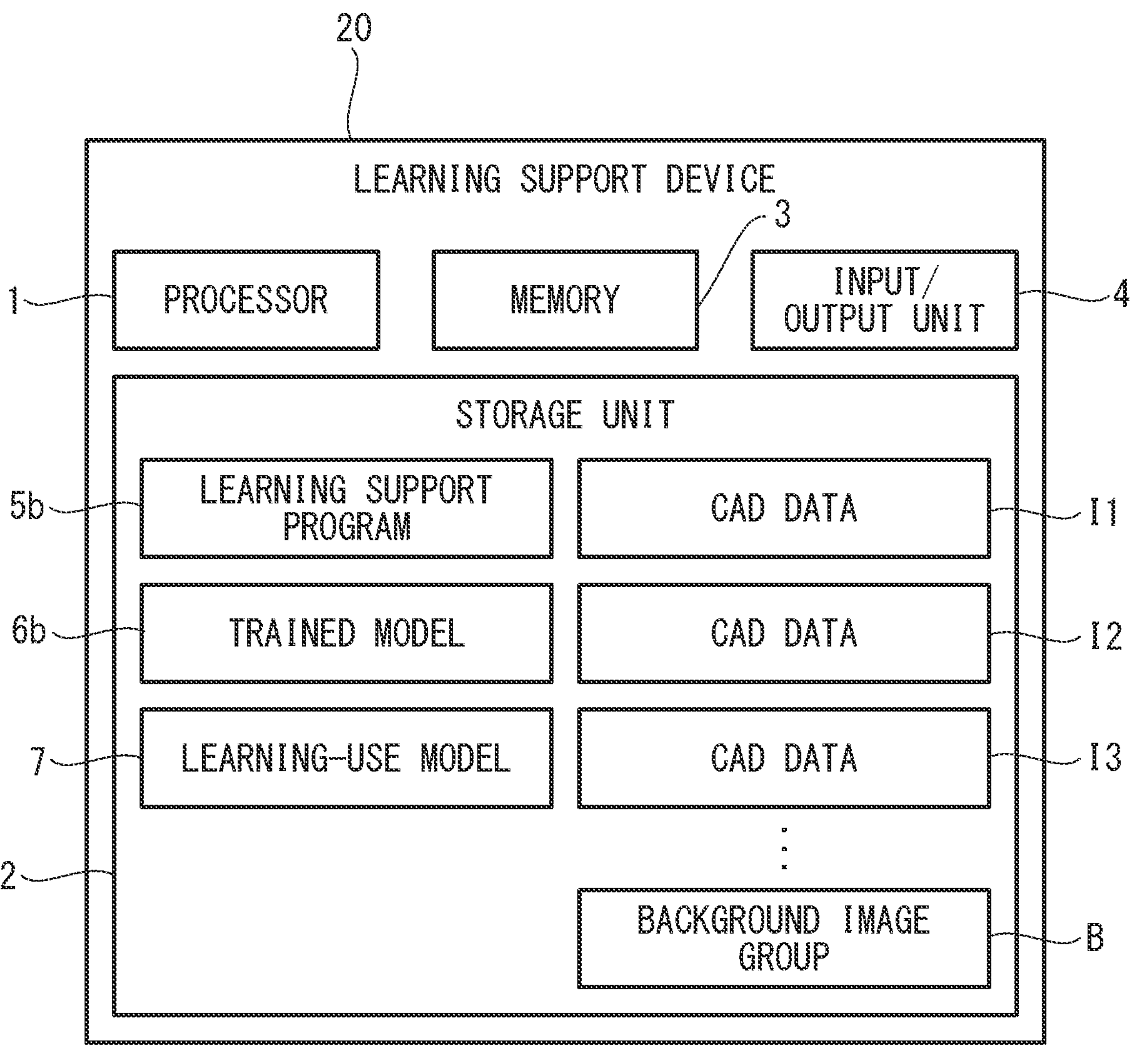
FIG. 9 is a block diagram showing a configuration of a learning support device according to a second embodiment.

As shown in FIG. 9, a learning support device 20 according to the present embodiment includes a processor 1, a storage unit 2, a memory 3, and an input/output unit 4.

The storage unit 2 stores a learning support program 5*b* that causes the processor 1 to perform the method for supporting learning according to the present embodiment, which will be described later. The storage unit 2 further stores a plurality of CAD (computer aided design) data I1, I2, I3, . . . a background image group B, and trained model 6*b*, all of which are necessary for the method for supporting learning.

The CAD data I1, I2, I3, . . . are respectively three-dimensional CAD data of three-dimensional models of treatment instruments 16*a*, 16*b*, 16*c*, . . . , and the treatment instruments 16*a*, 16*b*, 16*c*, . . . differ from each other.

In the same manner as the first embodiment, the trained model 6*b* is a CycleGAN that learns in advance the relationship between the color of a superimposed image and the color of a clinical image. The CycleGAN 6*b* is trained to form an image similar to the clinical image from the superimposed image D by using a plurality of superimposed images D that are experimentally formed from the CAD data I1, I2, I3, . . . and a plurality of clinical images. The CycleGAN 6*b* may be a GAN of another kind, such as a DCGAN (Deep Convolutional GAN), an LSGAN (Least Square GAN), a Wasserstein GAN, or a PGGAN (Progressive Growing GAN), for example.

Next, the method for supporting learning that is performed by the learning support device 20 will be described.

Figure 10:
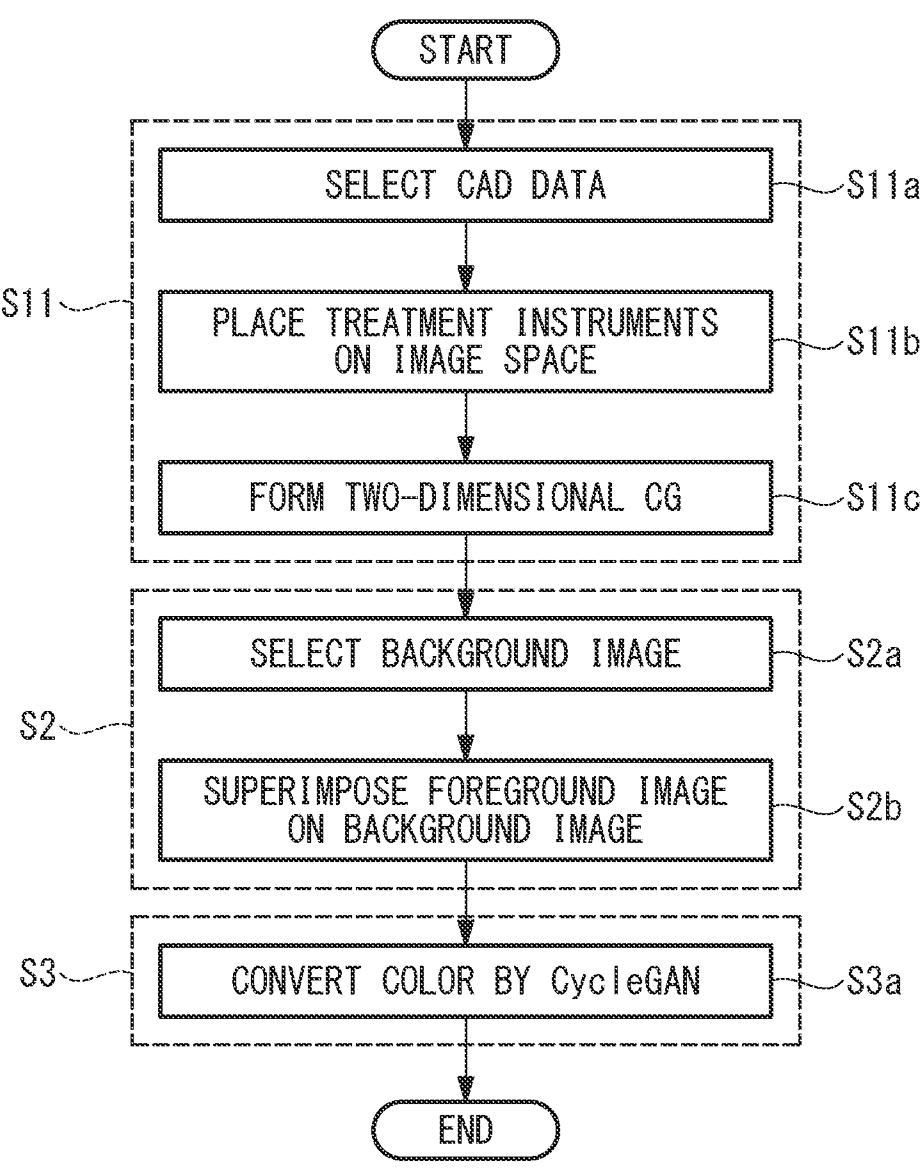
FIG. 10 is a flowchart of a method for supporting learning according to the second embodiment.

As shown in FIG. 10, the method for supporting learning according to the present embodiment includes step S11 of forming a foreground image C, step S2 of forming a superimposed image D in which the foreground image C is superimposed on a background image, and step S3 of forming a training image E by adjusting at least one of the hue, the saturation, or the brightness of the superimposed image D.

Figure 11:
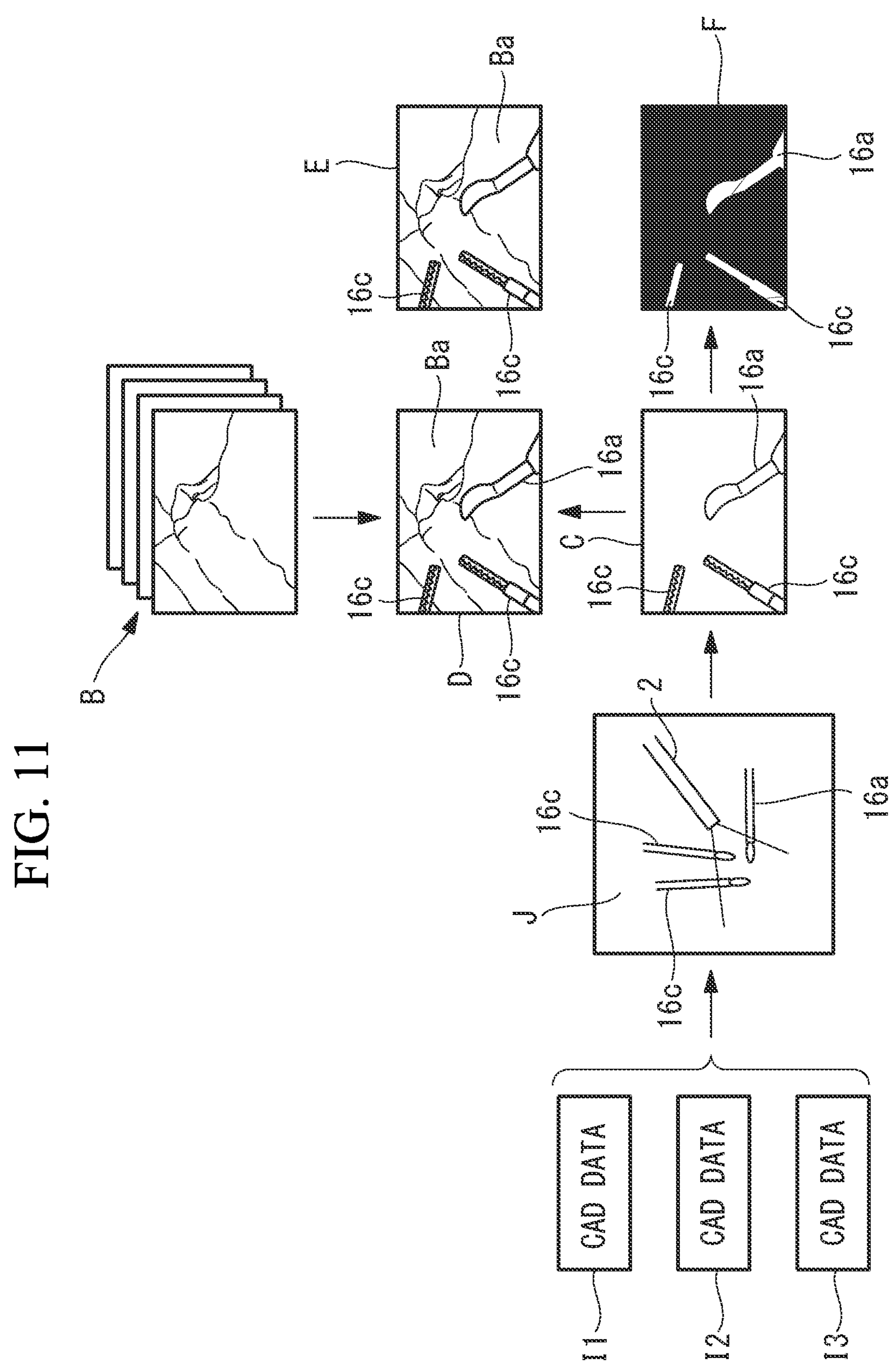
FIG. 11 is a diagram illustrating the method for supporting learning shown in FIG. 10.

FIG. 11 illustrates image processing in the method for supporting learning according to the present embodiment.

In step S11, the processor 1 forms the foreground image C containing at least one treatment instrument from the plurality of CAD data I1, I2, I3, . . . .

To be more specific, the processor 1 selects at least one set of CAD data from the plurality of CAD data I1, I2, I3, . . . (step S11*a*). In the case of the example shown in FIG. 11, two sets of CAD data I1, I3 are selected. The processor 1 may determine the kind and the number of treatment instruments according to placement data described in the first embodiment, and may select CAD data based on the determined kind and number of treatment instruments.

Next, the processor 1 places images of the treatment instruments 16*a*, 16*c* within a three-dimensional image region J, thus forming a three-dimensional CG image, the images of the treatment instruments 16*a*, 16*c* being three-dimensional models formed from CAD data I1, I3 (step S11*b*). The processor 1 may place treatment instruments in the image region J at random or according to the placement data.

Next, the processor 1 converts the three-dimensional CG image to two dimensions, thus forming the foreground image C being a two-dimensional CG image (step S11*c*).

Step S2 is as described in the first embodiment.

In step S3, the processor 1 inputs the superimposed image D to the CycleGAN 6*b*, and then obtains, as an output from the CycleGAN 6*b*, a training image E being an image in which the hue, the saturation, and the brightness of the treatment instruments 16*a*, 16*c*, and the organ within the superimposed image D are converted. That is, the CycleGAN 6*b* forms, from the superimposed image D, the training image E with reality, that is, the training image E in which the hue, the saturation, and the brightness of the treatment instruments 16*a*, 16*c*, and the organ are close to those in the clinical image.

By performing steps S11, S2, S3 a large number of times, the processor 1 can form a large number of training images E that differ from each other in the number, kind, position and orientation of treatment instruments.

As described above, according to the present embodiment, the training image E is formed from the CAD data I1, I2, I3, . . . and the background image group B, and a clinical image containing treatment instruments is not required.

Accordingly, it is possible to form a training image E for various treatment instruments, including a treatment instrument for which there are no or only a small number of clinical images and hence, it is possible to support formation of a learning model for various treatment instruments, including the treatment instrument for which there are no or only a small number of clinical images.

Further, according to the present embodiment, by adjusting the hue, the saturation, and the brightness of the treatment instruments within the superimposed image D based on the relationship, learned in advance, between the color of the superimposed image and the color of the clinical image, it is possible to form a training image E with reality, that is, a training image E with small deviation from the clinical image with respect to color. By learning such a training image E, it is possible to form a learning model with high recognition accuracy for treatment instruments within the clinical image and hence, recognition performance for treatment instruments within an endoscopic image during endoscopic surgery can be enhanced.

Further, according to the present embodiment, it is possible to form a training image E with high reality of both treatment instruments and the background.

Further, according to the present embodiment, the GAN 6*b* is used as means for adjusting the color of the superimposed image D and hence, it is possible to form, from CAD data I1, I2, I3, a training image E with high reality of treatment instruments.

It is also possible to easily prepare images necessary for training of the CycleGAN 6*b*.

In the present embodiment, the processor 1 adjusts the color of the superimposed image D. However, the processor 1 may adjust the color of the foreground image C instead of adjusting the color of the superimposed image D. This method is also able to form a training image E with reality close to the clinical image.

Figure 12:
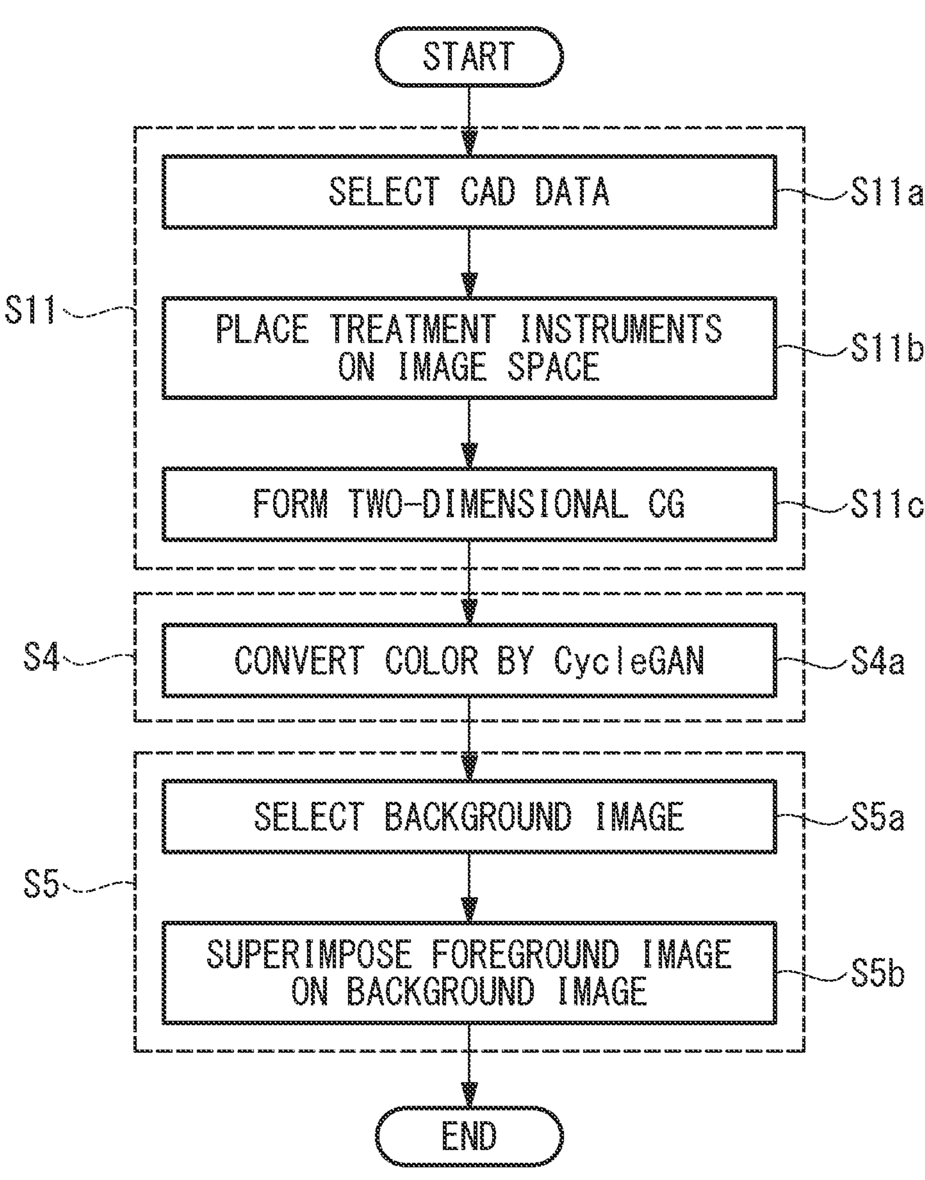
FIG. 12 is a flowchart of a modification of the method for supporting learning according to the second embodiment.
Figure 13:
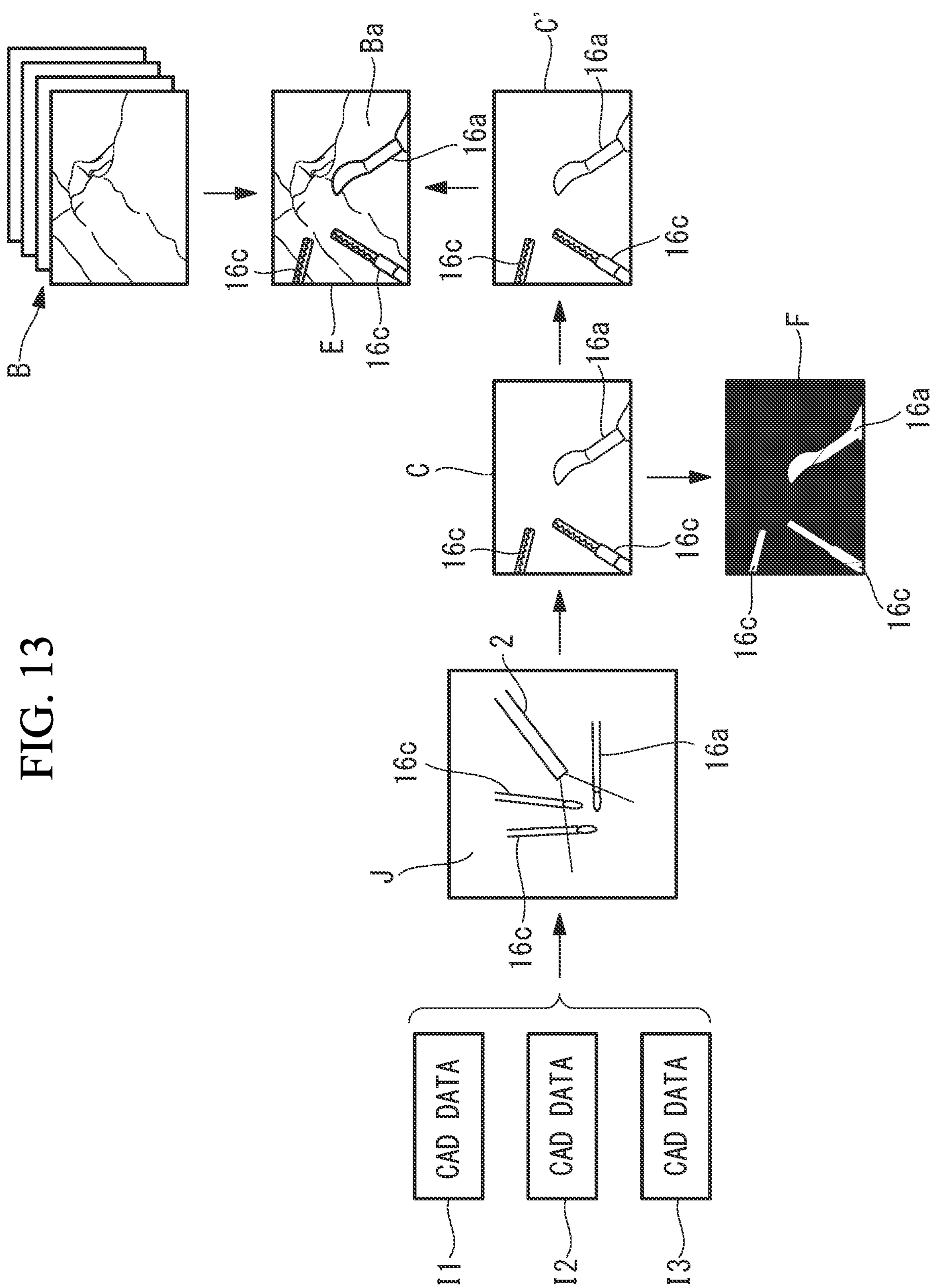
FIG. 13 is a diagram illustrating the method for supporting learning shown in FIG. 12.

FIG. 12 and FIG. 13 illustrate formation of the training image E in the case in which the color of the foreground image C is adjusted.

Instead of steps S2 and S3, the method for supporting learning shown in FIG. 12 includes step S4 of adjusting the color of the foreground image C, and step S5 of forming a training image E by superimposing the foreground image C' with the adjusted color on a background image.

In step S4, the processor 1 forms the image C' in which the colors of treatment instruments within the foreground image C are converted (adjusted) by the CycleGAN 6*b* (step S4*a*). In this case, the CycleGAN 6*b* is used that is trained to convert the colors of treatment instruments within the foreground image C to colors close to those of treatment instruments within the clinical image by using images of treatment instruments cut out from the clinical image.

Step S5 is as described in the first embodiment.

In the same manner as the first embodiment, the method for supporting learning of the present embodiment may also further include steps S6, S7, S8.

Third Embodiment

Next, a learning support device and a method for supporting learning according to a third embodiment of the present invention will be described.

The present embodiment differs from the first embodiment with respect to a point that the colors of treatment instruments within the foreground image C are adjusted by using an LUT (lookup table) instead of the GAN. In the present embodiment, components that are different from the components in the first embodiment will be described. Components identical to the corresponding components in the first embodiment are given the same reference symbols, and the description of such components will be omitted.

Figure 14:
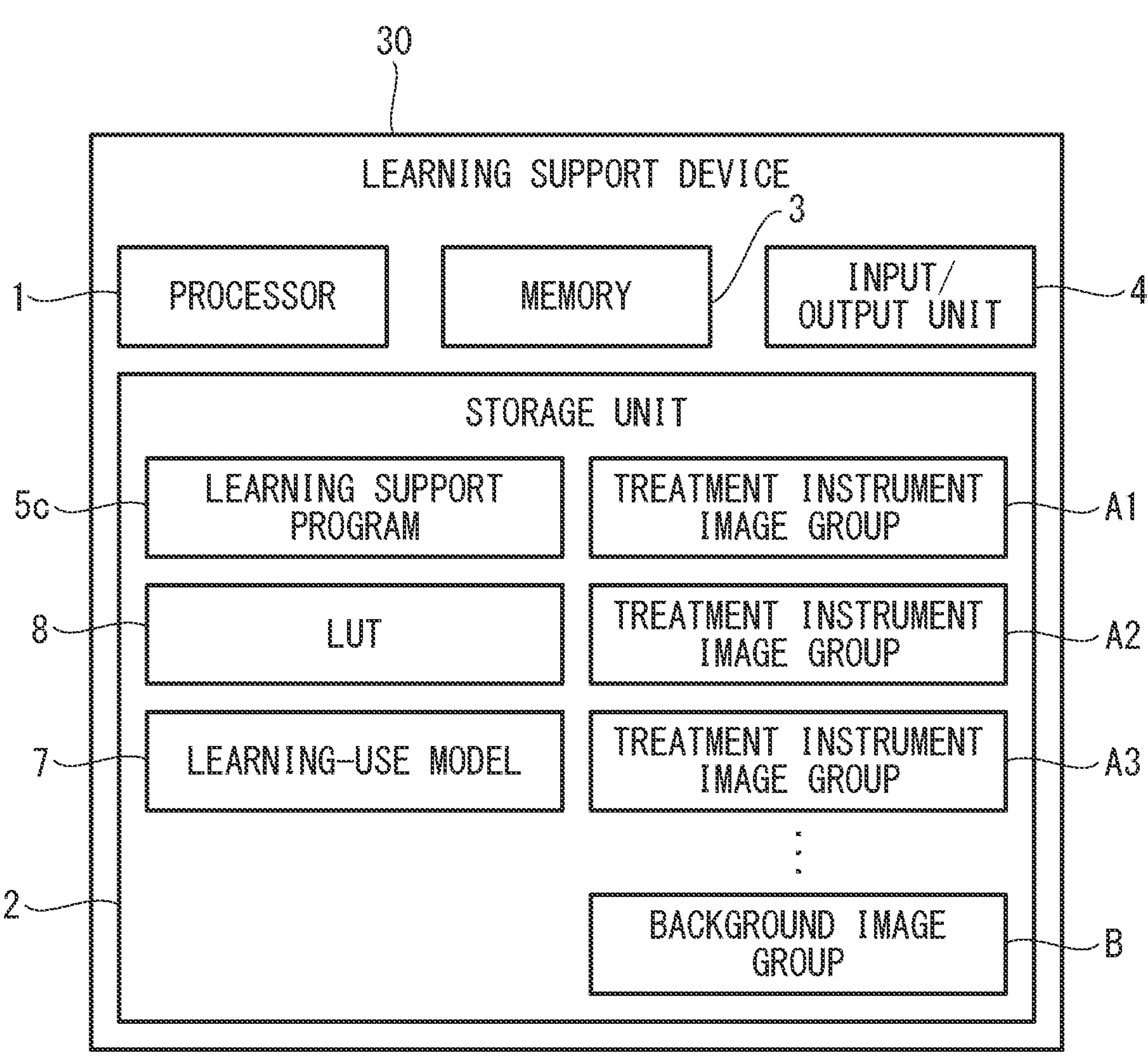
FIG. 14 is a block diagram showing a configuration of a learning support device according to a third embodiment.

As shown in FIG. 14, a learning support device 30 according to the present embodiment includes a processor 1, a storage unit 2, a memory 3, and an input/output unit 4.

The storage unit 2 stores a learning support program 5*c* that causes the processor 1 to perform the method for supporting learning according to the present embodiment, which will be described later. The storage unit 2 further stores image groups A1, A2, A3, . . . , B, and an LUT 8, all of which are necessary for the method for supporting learning.

The LUT 8 is a table showing the correspondence between the input value and the output value of color. The input value corresponds to the value of each pixel of the region of a treatment instrument within the foreground image C, and the output value corresponds to the value of each pixel of the region of a treatment instrument within the training image E. The LUT 8 is formed by the user, and is stored in advance in the storage unit 2.

The LUT 8 is formed by the following method.

A color clinical image containing treatment instruments is prepared, and the regions of the treatment instruments are extracted from the clinical image, and are then transformed into grayscale. Each pixel of a clinical image has an RGB value (Vr, Vg, Vb), and each pixel of the region of a treatment instrument that is transformed into grayscale has a brightness value U.

Next, the LUT 8 is formed that converts the brightness value U of gray scale to an RGB value of color based on the brightness value U and the RGB value (Vr, Vg, Vb) of each pixel at the same position. The input value is a brightness value U, and the output value is an RGB value (Vr, Vg, Vb).

Next, the method for supporting learning that is performed by the learning support device 30 will be described.

Figure 15:
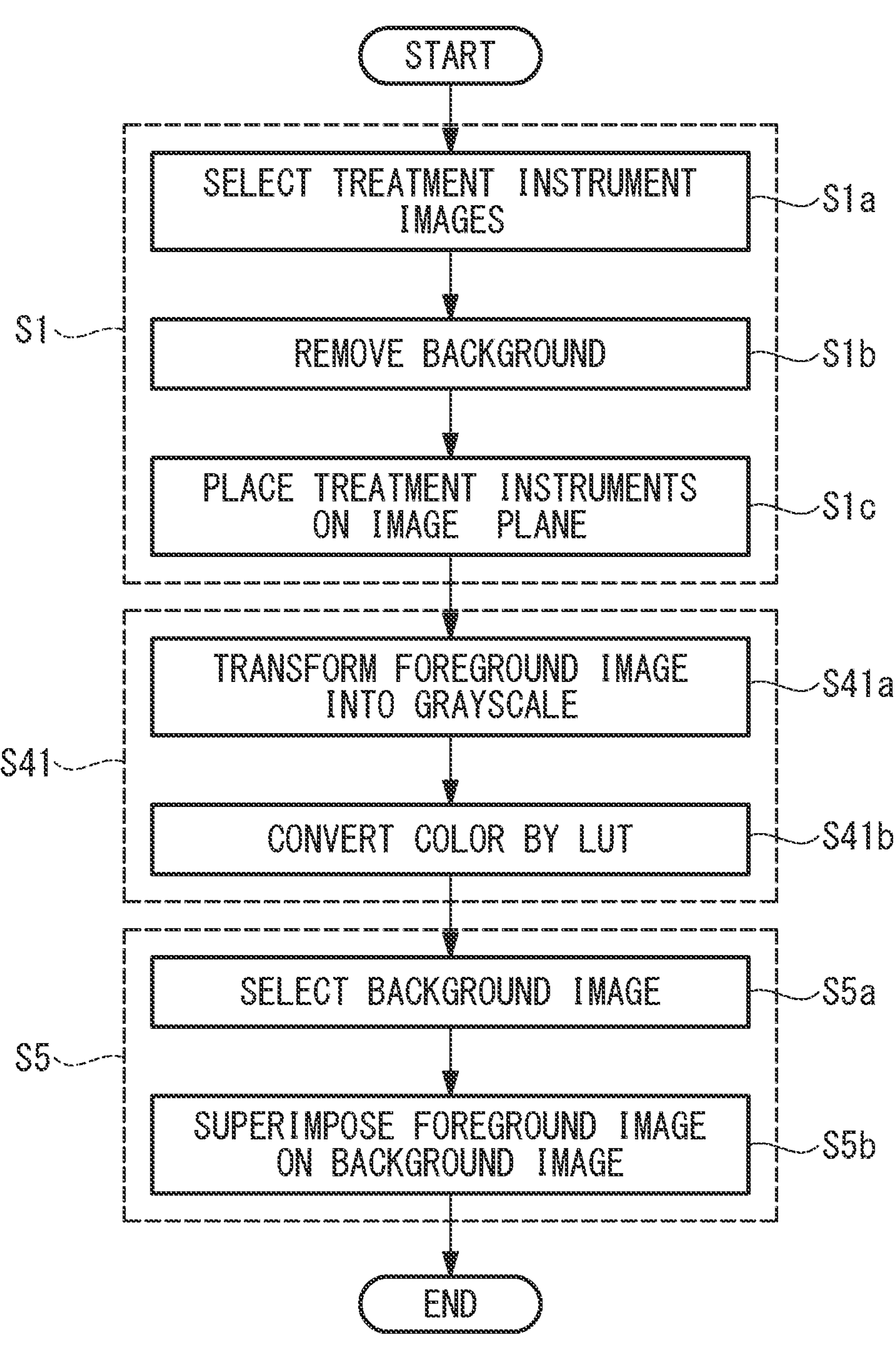
FIG. 15 is a flowchart of a method for supporting learning according to the third embodiment.

As shown in FIG. 15, the method for supporting learning according to the present embodiment includes step S1 of forming a foreground image C, step S41 of adjusting the color of the foreground image C, and step S5 of forming a training image E by superimposing a foreground image C' with the adjusted color on a background image.

Step S1 is as described in the first embodiment.

In step S41, the processor 1 transforms the foreground image C into grayscale to form a gray scale image (step S41*a*). Next, the processor 1 converts the brightness value U of each pixel of the gray scale image to the RGB value (Vr, Vg, Vb) based on the LUT 8, thus forming a foreground image C' in which the colors of the treatment instruments are adjusted (step S41*b*). The treatment instruments within the foreground image C' have hue and saturation close to those of treatment instruments within the clinical image.

Step S5 is as described in the first embodiment.

By performing steps S1, S41, S5 a large number of times, the processor 1 can form a large number of training images E that differ from each other in the number, kind, position and orientation of treatment instruments.

As described above, according to the present embodiment, the training image E is formed from the image groups A1, A2, A3, . . . , B, and a clinical image containing treatment instruments is not required. Accordingly, it is possible to form a training image E for various treatment instruments, including a treatment instrument for which there are no or only a small number of clinical images and hence, it is possible to support formation of a learning model for various treatment instruments, including the treatment instrument for which there are no or only a small number of clinical images.

Further, according to the present embodiment, by adjusting the hue and the saturation of the treatment instruments within the foreground image C by using the LUT 8 formed in advance based on the color of the clinical image, it is possible to form a training image E with reality, that is, a training image E with small deviation from the clinical image with respect to color. By learning such a training image E, it is possible to form a learning model with high recognition accuracy for treatment instruments within the clinical image and hence, recognition performance for treatment instruments within an endoscopic image during endoscopic surgery can be enhanced.

Further, according to the present embodiment, the foreground image C is transformed into grayscale and, subsequently, the brightness value is converted to the RGB value based on the LUT 8. Thus, it is possible to remove the influence of the hue and the saturation of treatment instruments within the foreground image C on conversion of color and hence, the colors of the treatment instruments within the foreground image C can be adjusted with high accuracy to colors even closer to the colors of treatment instruments within the clinical image.

In the same manner as the first embodiment, the method for supporting learning of the present embodiment may also further include steps S6, S7, S8.

Fourth Embodiment

Next, a learning support device and a method for supporting learning according to a fourth embodiment of the present invention will be described.

The present embodiment differs from the first embodiment with respect to a point that the color of a superimposed image is adjusted by correcting an HSV value instead of the GAN. In the present embodiment, components that are different from the components in the first embodiment will be described. Components identical to the corresponding components in the first embodiment are given the same reference symbols, and the description of such components will be omitted.

Figure 16:
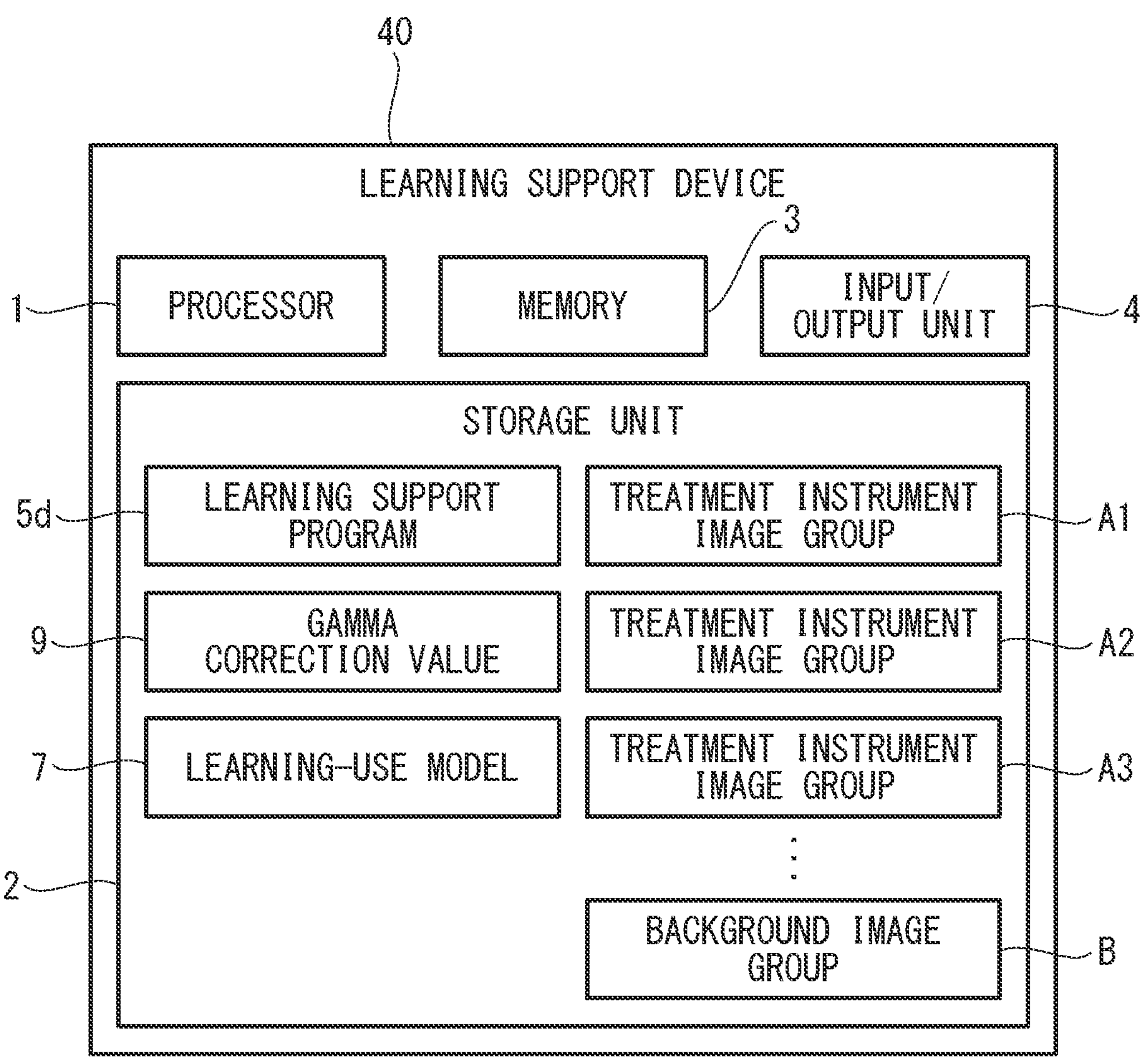
FIG. 16 is a block diagram showing a configuration of a learning support device according to a fourth embodiment.

As shown in FIG. 16, a learning support device 40 according to the present embodiment includes a processor 1, a storage unit 2, a memory 3, and an input/output unit 4.

The storage unit 2 stores a learning support program 5*d* that causes the processor 1 to perform the method for supporting learning according to the present embodiment, which will be described later. The storage unit 2 further stores image groups A1, A2, A3, . . . , B, and a gamma correction value 9, all of which are necessary for the method for supporting learning.

Next, the method for supporting learning that is performed by the learning support device 40 will be described.

Figure 17:
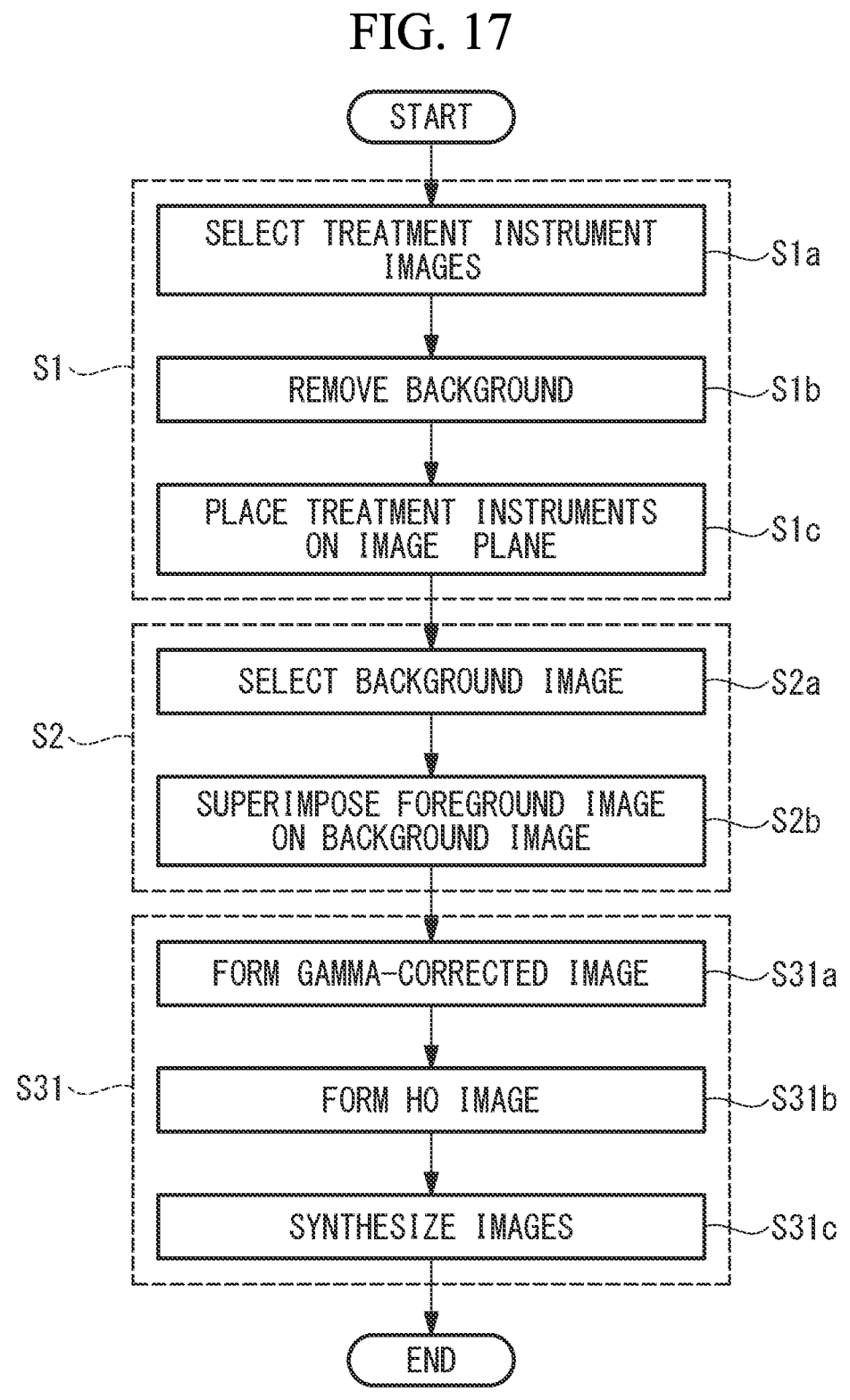

As shown in FIG. 17, the method for supporting learning according to the present embodiment includes step S1 of forming a foreground image C, step S2 of forming a superimposed image D in which the foreground image C is superimposed on a background image, and step S31 of forming a training image E by adjusting the color of the superimposed image D.

Steps S1, S2 are as described in the first embodiment.

In step S31, the processor 1 forms the training image E from the superimposed image D based on a gamma correction value 9.

To be more specific, the processor 1 forms a gamma-corrected image and a hue-corrected image from the superimposed image D based on the gamma correction value 9 (step S31*a*, S31*b*).

Figure 18A:
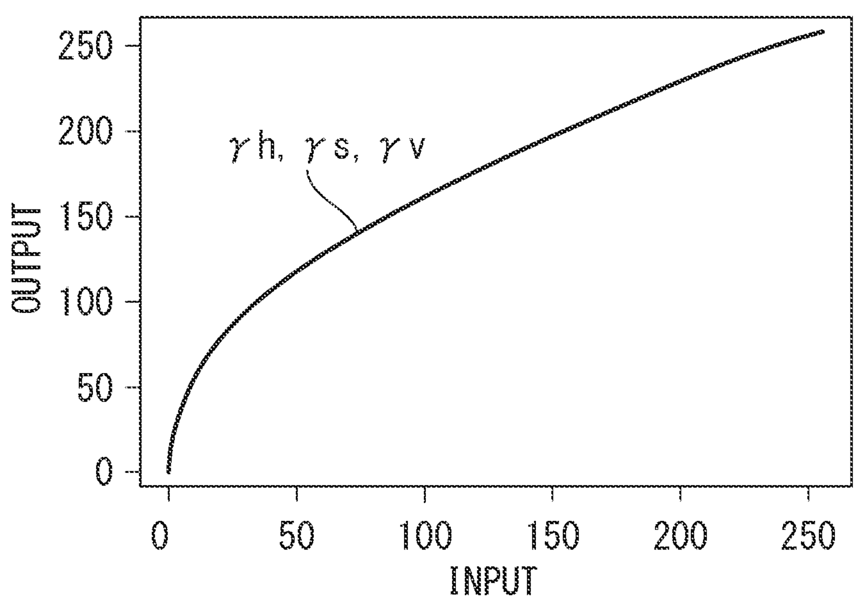
FIG. 18A is a graph illustrating gamma correction value.

The gamma correction value 9 includes a gamma correction value γh for hue, a gamma correction value γs for saturation, and a gamma correction value γv for brightness. A gamma-corrected image is an image in which at least one gamma value of the hue, the saturation, and the brightness of the superimposed image D is corrected to a correction value γh, γs, or γv. FIG. 18A shows an example of a gamma curve of a gamma-corrected image.

Figure 18B:
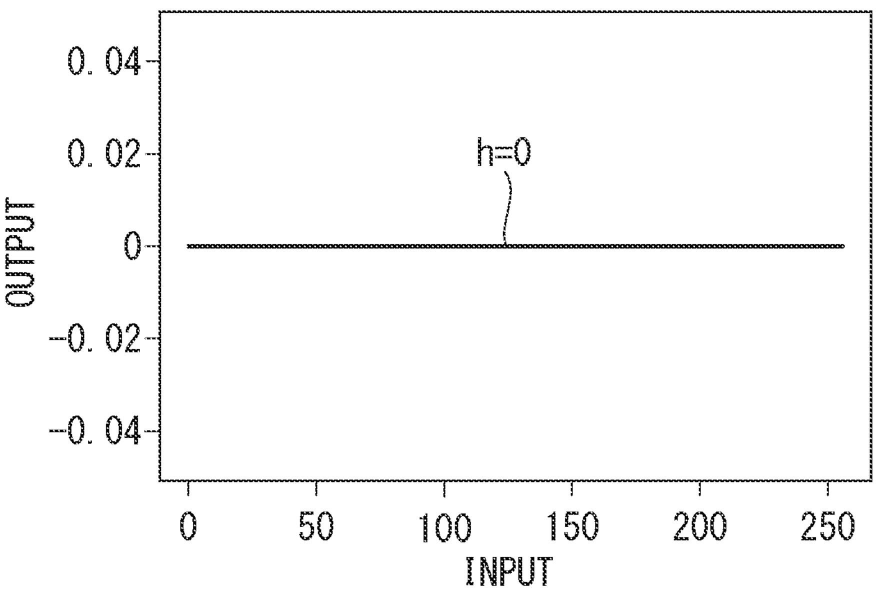
FIG. 18B is a graph illustrating H0 correction.

A hue-corrected image is an image in which all hue values of the superimposed image D are converted to zero (hereinafter also referred to as "H0 image"). FIG. 18B shows the hue value of a H0 image.

Figure 19A:
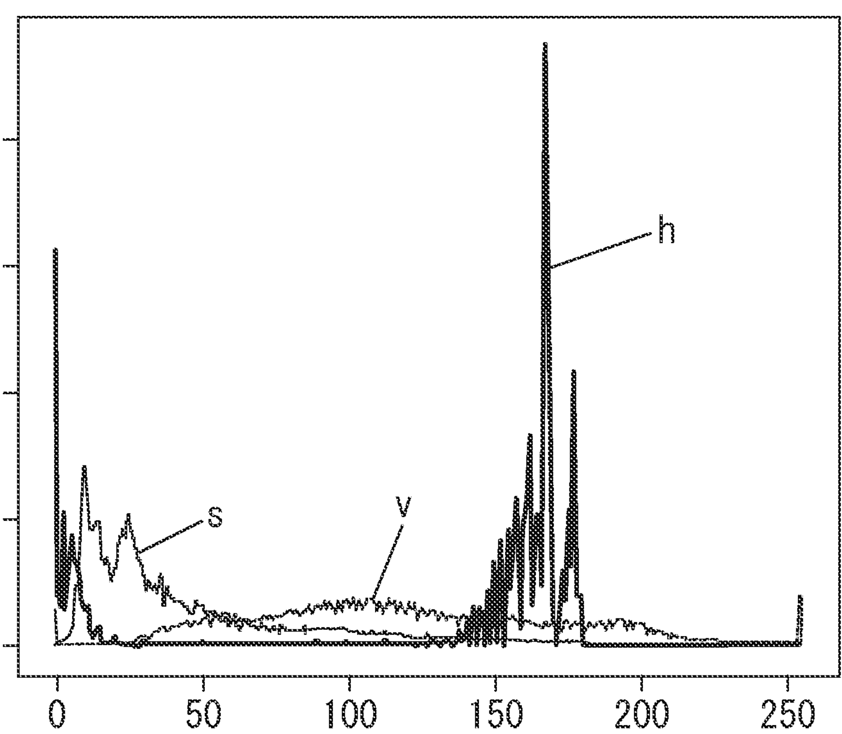
FIG. 19A is a graph showing an example of an HSV histogram of a clinical image.
Figure 19B:
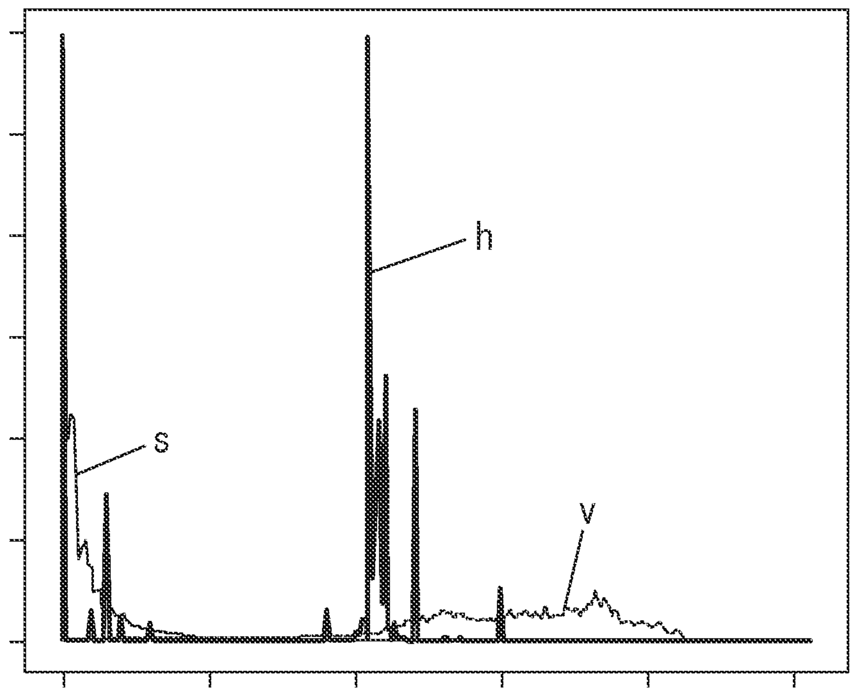
FIG. 19B is a graph showing an example of the HSV histogram of a superimposed image.

FIG. 19A shows an example of an HSV histogram of the clinical image, and FIG. 19B shows an example of the HSV histogram of the superimposed image D.

As can be understood from FIG. 19A and FIG. 19B, the peak positions of hue (h), saturation(s), and brightness (v) of the superimposed image D differ from the peak positions of hue (h), saturation(s), and brightness (v) of the clinical image. Based on the HSV histogram of the clinical image and the HSV histogram of the superimposed image D that is experimentally formed, correction values γh, γs, γv are determined such that the HSV histogram of the superimposed image D approaches the HSV histogram of the clinical image. For example, the gamma correction value γh of hue is determined such that the peak position of the hue of the superimposed image D coincides or substantially coincides with the peak position of the hue of the clinical image. The gamma correction value γs of saturation is determined such that the peak position of the saturation of the superimposed image D coincides or substantially coincides with the peak position of the saturation of the clinical image. The gamma correction value γv of brightness is determined such that the peak position of the brightness of the superimposed image D coincides or substantially coincides with the peak position of the brightness of the clinical image. In an preferred example, γh=2.1, γs=1.3, and γv=1.0.

Next, the processor 1 synthesizes the superimposed image D, the gamma-corrected image, and the H0 image to form a training image E (step S31*c*). To be more specific, the processor 1 combines values of pixels of the superimposed image D, the gamma-corrected image, and the H0 image at the same position at a predetermined ratio. The predetermined ratio may be superimposed image:gamma-corrected image:hue-corrected image=0.125:0.5:0.375, for example.

By performing steps S1, S2, S31 a large number of times, the processor 1 can form a large number of training images E that differ from each other in the number, kind, position and orientation of treatment instruments.

As described above, according to the present embodiment, the training image E is formed from the image groups A1, A2, A3, . . . , B, and a clinical image containing treatment instruments is not required. Accordingly, it is possible to form a training image E for various treatment instruments, including a treatment instrument for which there are no or only a small number of clinical images and hence, it is possible to support formation of a learning model for various treatment instruments, including the treatment instrument for which there are no or only a small number of clinical images.

Further, according to the present embodiment, by adjusting the hue, the saturation, and the brightness of the treatment instruments within the superimposed image D based on the relationship, which is measured in advance, between the color of the superimposed image and the color of the clinical image, it is possible to form a training image E with reality, that is, a training image E with small deviation from the clinical image with respect to color. By learning such a training image E, it is possible to form a learning model with high recognition accuracy for treatment instruments within the clinical image and hence, recognition performance for treatment instruments within an endoscopic image during endoscopic surgery can be enhanced.

In the present embodiment, the processor 1 adjusts the color of the superimposed image D. However, the processor 1 may adjust the color of the foreground image C instead of adjusting the color of the superimposed image D. That is, instead of steps S2 and S31, the method for supporting learning may include a step of adjusting the color of the foreground image C based on the gamma correction value 9, and a step of forming a training image E by superimposing the foreground image C' with the adjusted color on a background image.

In the same manner as the first embodiment, the method for supporting learning of the present embodiment may also further include steps S6, S7, S8.

Fifth Embodiment

Next, a learning support device and an endoscope system according to a fifth embodiment of the present invention will be described.

Figure 20:
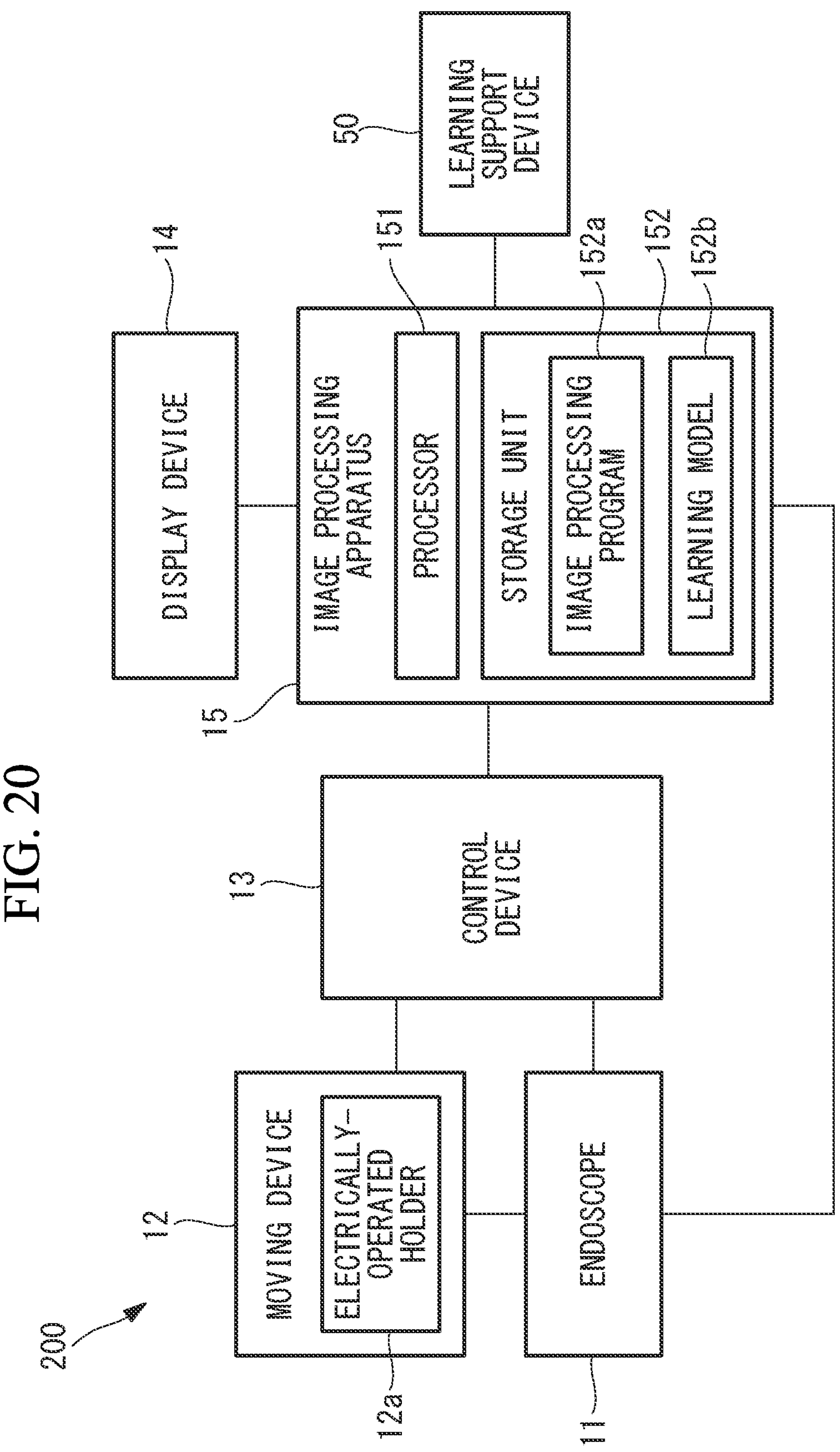
FIG. 20 is a block diagram showing a configuration of an endoscope system according to a fifth embodiment.

As shown in FIG. 20, an endoscope system 200 according to the present embodiment includes an endoscope 11, a moving device 12 that changes the position and the orientation of the endoscope 11, a control device 13 that controls the endoscope 11 and the moving device 12, a display device 14, an image processing apparatus 15, and a learning support device 50.

In the same manner as the endoscope system 100 described in the first embodiment, the endoscope system 200 is used for laparoscopic surgery, for example.

The endoscope 11 includes a camera including an imaging element, such as a CCD image sensor or a CMOS image sensor, and obtains an endoscopic image G in a subject X by the camera. The camera may be a three-dimensional camera that obtains stereo images.

The endoscopic image G is transmitted to the display device 14 via the control device 13 or the image processing apparatus 15 from the endoscope 11, and is displayed on the display device 14. The display device 14 is an arbitrary display, such as a liquid crystal display or an organic EL display.

The moving device 12 includes an electrically-operated holder 12*a* formed of an articulated robot arm, and is controlled by the control device 13. The endoscope 11 is held at a distal end portion of the electrically-operated holder 12*a*, and the position of the distal end of and the orientation of the endoscope 11 are three-dimensionally changed by the action of the electrically-operated holder 12*a*. The moving device 12 may be another mechanism that can change the position and the orientation of the distal end of the endoscope 11, such as a bent portion provided at the distal end portion of the endoscope 11.

The control device 13 includes a processor, a storage unit, a memory, an input/output interface, and the like.

As described in the first embodiment, the control device 13 performs tracking control that causes the field of view of the endoscope 11 to track a predetermined treatment instrument 16 as the target to be tracked. For example, in the tracking control, the control device 13 obtains the three-dimensional position of the distal end of the treatment instrument 16 from a stereo endoscopic image G, and controls the moving device 12 based on the position of the distal end.

The image processing apparatus 15 includes a processor 151, a storage unit 152, a memory, an input/output unit, and the like.

The storage unit 152 is a computer readable non-transitory recording medium, and may be a hard disk drive, an optical disk, or a flash memory, for example. The storage unit 152 stores an image processing program 152*a* that causes the processor 151 to perform a method for processing an image, which will be described later.

In the same manner as the learning support device 10, the learning support device 50 includes a processor 1, a storage unit 2, a memory 3, and an input/output unit 4. The storage unit 2 stores a learning support program that causes the processor 1 to perform the method for supporting learning according to the present embodiment, which will be described later. The method for supporting learning of the present embodiment is based on any one of the methods for supporting learning described in the first to fourth embodiments. Accordingly, the storage unit 2 stores any of data A1, A2, A3, . . . , B, I1, I2, I3, . . . , 6*a*, 6*b*, 8, and 9 depending on the method for supporting learning of the present embodiment.

Next, the method for supporting learning that is performed by the learning support device 50 will be described by taking the method for supporting learning of the first embodiment as an example.

Figure 21A:
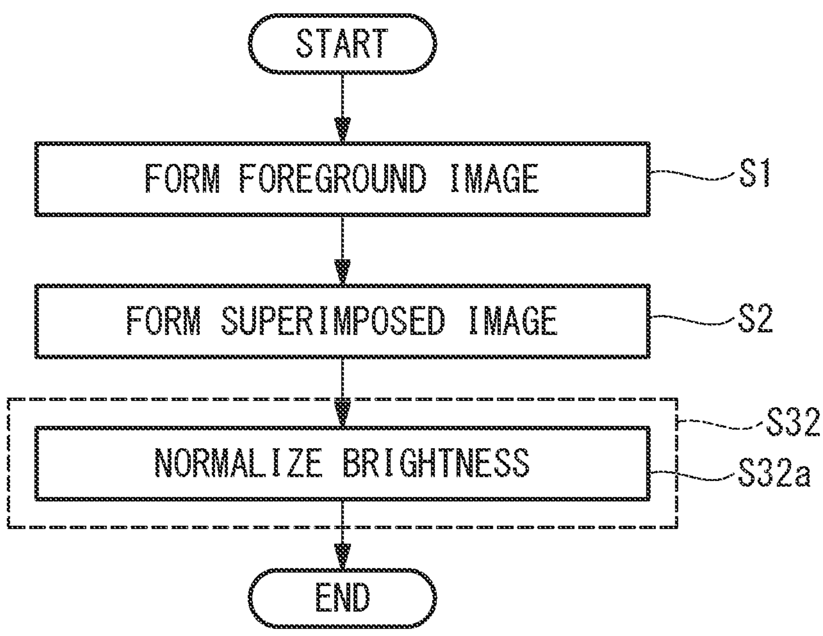
FIG. 21A is a flowchart of a method for supporting learning according to the fifth embodiment.

As shown in FIG. 21, the method for supporting learning according to the present embodiment includes step S1 of forming a foreground image C, step S2 of forming a superimposed image D in which the foreground image C is superimposed on a background image, and step S32 of forming a training image E by adjusting the color of the superimposed image D.

Steps S1, S2 are as described in the first embodiment.

Figure 22:
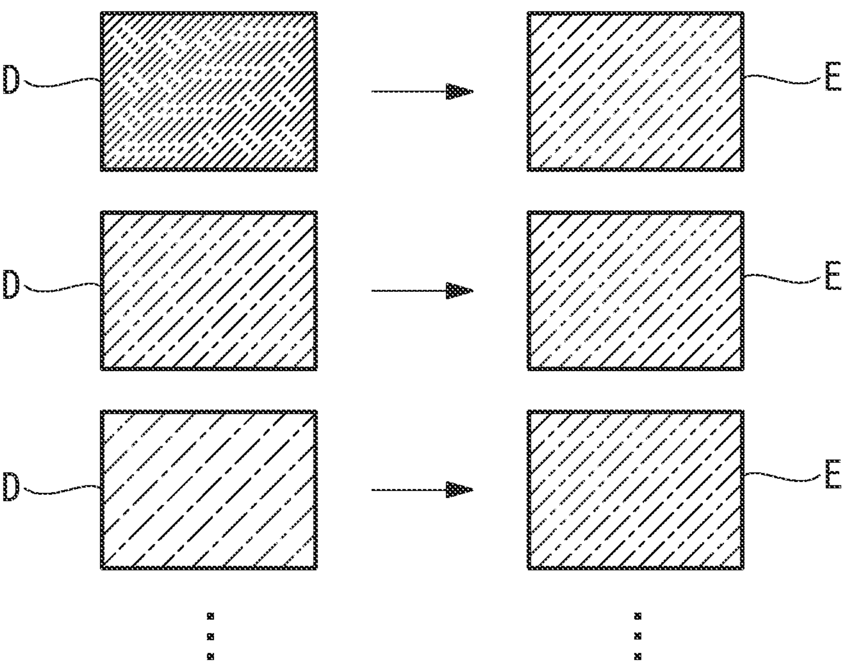
FIG. 22 is a diagram illustrating normalization of brightness of a superimposed image.

As shown in FIG. 22, superimposed images D formed from different treatment instrument images with a background image may differ from each other in brightness. In step S32, the processor 1 normalizes the brightness of the superimposed image D, thus forming a training image E (step S32*a*). Normalizing brightness reduces variation in brightness of the training image E caused by a difference in brightness of the superimposed image D. Brightness is normalized by a known method, such as by flattening the histogram of the brightness of the superimposed image D, or by statistically normalizing the brightness of the superimposed image D, for example. In FIG. 22, a difference in density of hatching represents a difference in brightness.

By performing steps S1, S2, S32 a large number of times, the processor 1 can form a large number of training images E that differ from each other in the number, kind, position and orientation of treatment instruments. As shown in FIG. 22, by normalizing the brightness of the superimposed images D, a large number of training images E with less variation in brightness are formed.

The processor 1 may normalize the brightness of the foreground image C instead of the superimposed image D. In this case, the processor 1 forms a training image E by superimposing the foreground image C' with the adjusted brightness on a background image. A large number of training images E formed by this method are substantially equal to each other in brightness of the region of the treatment instrument.

A large number of training images E are used for formation of a learning model, and a formed learning model 152*b* is stored in the storage unit 152 of the image processing apparatus 15.

A learning model may be formed by the learning support device 50. That is, the method for supporting learning of the present embodiment may further include steps S6, S7, S8. Alternatively, a learning model may be formed by a device other than the learning support device 50.

Next, the method for processing an image that is performed by the image processing apparatus 15 during endoscopic surgery will be described.

Figure 21B:
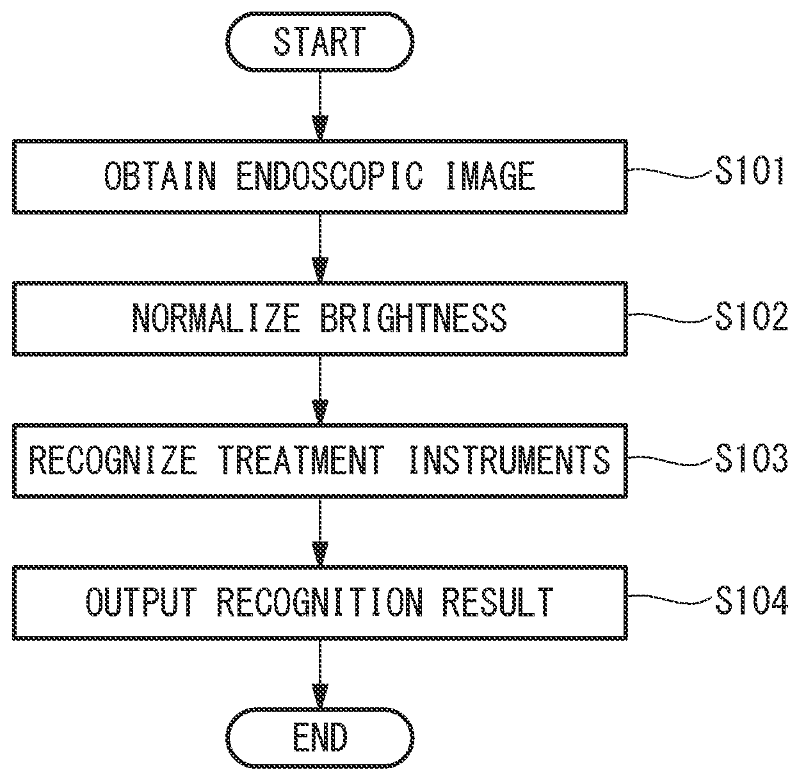
FIG. 21B is a flowchart of a method for processing an image according to the fifth embodiment.

As shown in FIG. 21B, the method for processing an image according to the present embodiment includes step S101 of obtaining an endoscopic image, step S102 of normalizing the brightness of the endoscopic image G, step S103 of recognizing treatment instruments 16 within the endoscopic image G based on the learning model, and step S104 of outputting the recognition result to the display device 14.

During endoscopic surgery, the endoscopic image G is sequentially input to the image processing apparatus 15 from the endoscope 11.

The processor 151 obtains the endoscopic image G input to the image processing apparatus 15 (step S101), and normalizes the brightness of the endoscopic image G by using the same method as the method used for normalizing the brightness of the superimposed image D in step S32 (step S102).

Next, the processor 151 inputs the endoscopic image G with the normalized brightness to the learning model 152*b* to obtain the positions of the regions of the recognized treatment instruments as the recognition result from the learning model 152*b* (step S103).

Figure 23:
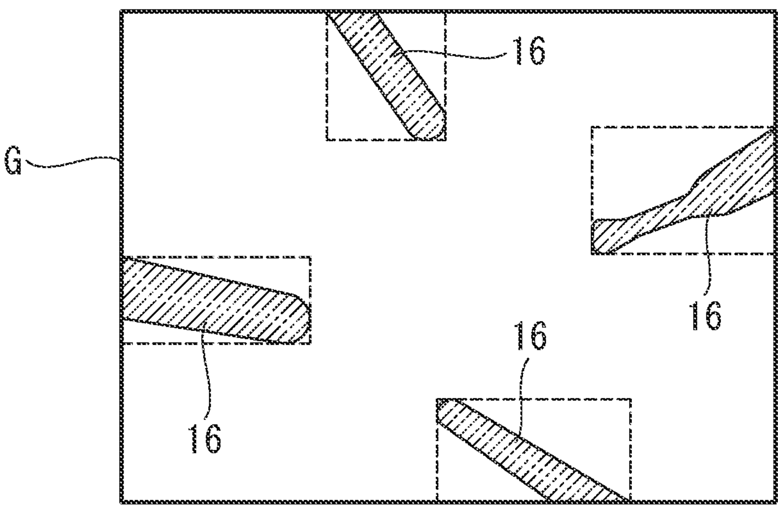
FIG. 23 is a diagram showing an example of a recognition result with respect to treatment instruments.

Next, the processor 151 displays the recognition result with respect to the treatment instruments 16 on the display device 14 (step S104). For example, as shown in FIG. 23, the processor 151 may superimpose color markers on the regions of the recognized treatment instruments 16 within the endoscopic image G, or may superimpose frames that surround the recognized treatment instruments 16 on the endoscopic image G.

The recognition result with respect to the treatment instruments may be used for tracking control performed by the control device 13.

In the case in which there is a variation in brightness between a plurality of training images E, it is necessary to perform learning by taking into account the variation in brightness, so that a large number of training images E are necessary to form a learning model.

According to the present embodiment, a plurality of training images E having a small difference in brightness are formed. Thus, it is possible to reduce the number of training images E necessary to form a learning model.

Further, by normalizing the brightness of the endoscopic image G used to recognize treatment instruments, by the same method as the training image E, it is possible to enhance recognition accuracy for treatment instruments within the endoscopic image G.

In the present embodiment, the learning support device 50 is separated from the control device 13 and the image processing apparatus 15. However, instead of adopting such a configuration, the learning support device 50 may be integrally formed with at least one of the control device 13 or the image processing apparatus 15. For example, the learning support device 50 and the image processing apparatus 15 may be incorporated in the control device 13.

The embodiments of the present invention and modifications of the embodiments have been described heretofore. However, the present invention is not limited to the above, and may be suitably modified without departing from the gist of the present invention.

In each of the above-mentioned embodiments and the modifications, the sample image group is formed of the treatment instrument image groups A1, A2, A3, . . . and the background image group B. However, the sample image group may further include an image group of another object. Another object may be an artifact such as gauze or a Nelaton tube, or an organ, for example.

The invention claimed is:

1. A learning support device that supports formation of a learning model that recognizes a treatment instrument within an endoscopic image, the learning support device comprising a processor, wherein the processor is configured to:
- form a foreground image containing at least one treatment instrument by placing an image of the at least one treatment instrument within an image region;
- form a superimposed image by superimposing the foreground image on a background image; and
- form a training image by:
  - forming a gamma-corrected image from the superimposed image;
  - forming a hue-corrected image from the superimposed image; and
  - forming the training image by synthesizing the superimposed image, the gamma-corrected image, and the hue-corrected image, wherein:
    - the gamma-corrected image is an image in which a gamma value of at least one of a hue, a saturation and a brightness of the superimposed image is corrected, and
    - the hue-corrected image is an image in which all hue values of the superimposed image are converted to zero.

2. The learning support device according to claim 1, wherein the processor is further configured to normalize the brightness of the superimposed image to reduce a difference in brightness between the superimposed image.

3. The learning support device according to claim 1, wherein the superimposed image, the gamma-corrected image, and the hue-corrected image are synthesized at a ratio of 0.125:0.5:0.375.

4. The learning support device according to claim 1, further comprising a storage unit configured to store a learning-use model, wherein the processor is further configured to cause the learning-use model to learn the training image to form the learning model that recognizes the treatment instrument within the endoscopic image.

5. An endoscope system comprising:
- the learning support device according to claim 4;
- an endoscope configured to acquire at least one endoscopic image; and
- an image processing apparatus including a processor and a storage unit configured to store the learning model, wherein the processor of the image processing apparatus is configured to input the endoscopic image to the learning model to obtain, from the learning model, a recognition result with respect to the treatment instrument within the endoscopic image.

6. The endoscope system according to claim 5, further comprising a display device, wherein the processor of the image processing apparatus is further configured to display the recognition result on the display device.

7. A learning support device that supports formation of a learning model that recognizes a treatment instrument within an endoscopic image, the learning support device comprising a processor, wherein the processor is configured to:

form a foreground image containing at least one treatment instrument by placing an image of the at least one treatment instrument within an image region; and form a training image by:

forming a gamma-corrected image from the foreground image;

forming a hue-corrected image from the foreground image; and forming the training image by synthesizing the foreground image, the gamma-corrected image, and the hue-corrected image, wherein:

the gamma-corrected image is an image in which a gamma value of at least one of a hue, a saturation and a brightness of the foreground image is corrected, and the hue-corrected image is an image in which all hue values of the foreground image are converted to zero.

8. The learning support device according to claim 7, wherein adjusting the at least one of the hue, the saturation, or the brightness of the foreground image includes converting a value of each pixel of the foreground image based on a LUT (lookup table).

9. A method for supporting learning, the method supporting formation of a learning model that recognizes a treatment instrument within an endoscopic image, the method comprising:

forming a foreground image containing at least one treatment instrument by placing an image of the at least one treatment instrument within an image region;

forming a superimposed image by superimposing the foreground image on a background image; and forming a training image by;

forming a gamma-corrected image from the superimposed image;

forming a hue-corrected image from the superimposed image; and forming the training image by synthesizing the superimposed image, the gamma-corrected image, and the hue-corrected image, wherein:

the gamma-corrected image is an image in which a gamma value of at least one of a hue, a saturation and a brightness of the superimposed image is corrected, and the hue-corrected image is an image in which all hue values of the superimposed image are converted to zero.

* * * * *